US009833198B2

(12) United States Patent
Stapleton

(10) Patent No.: US 9,833,198 B2
(45) Date of Patent: Dec. 5, 2017

(54) SYSTEM AND METHOD FOR OBTAINING AN OBJECTIVE DENTAL HEALTH ANALYSIS

(71) Applicant: Francis J. Stapleton, Pleasantville, NY (US)

(72) Inventor: Francis J. Stapleton, Pleasantville, NY (US)

( * ) Notice: Subject to any disclaimer, the term of this patent is extended or adjusted under 35 U.S.C. 154(b) by 367 days.

(21) Appl. No.: 14/613,534

(22) Filed: Feb. 4, 2015

(65) Prior Publication Data

US 2016/0220196 A1   Aug. 4, 2016

(51) Int. Cl.
*A61B 5/00* (2006.01)
*A61B 5/11* (2006.01)
*A61B 34/10* (2016.01)

(52) U.S. Cl.
CPC ........... *A61B 5/7282* (2013.01); *A61B 5/1111* (2013.01); *A61B 5/4547* (2013.01); *A61B 34/10* (2016.02); *A61B 5/0022* (2013.01); *A61B 5/742* (2013.01)

(58) Field of Classification Search
CPC ... A61B 5/7282; A61B 5/1111; A61B 5/4547; A61B 5/0022; A61B 5/742; A61B 34/10
See application file for complete search history.

(56) References Cited

U.S. PATENT DOCUMENTS

| | | | |
|---|---|---|---|
| 5,692,501 A * | 12/1997 | Minturn | A61B 5/00 600/301 |
| 5,752,827 A * | 5/1998 | Baron | A61C 19/043 433/29 |
| 5,755,571 A * | 5/1998 | Companion | A61C 19/043 33/514 |
| 8,267,689 B2 | 9/2012 | Martin et al. | |
| 2003/0011191 A1 * | 1/2003 | Tosaki | A61B 5/00 283/115 |
| 2003/0053673 A1 * | 3/2003 | Dewaele | G06F 19/3431 382/132 |
| 2004/0034289 A1 * | 2/2004 | Teller | A61B 5/02055 600/300 |
| 2006/0154210 A1 * | 7/2006 | Martin | A61B 5/00 433/215 |
| 2007/0184411 A1 | 8/2007 | Stapleton | |
| 2010/0015575 A1 * | 1/2010 | Martin | G06F 19/3487 433/215 |

(Continued)

*Primary Examiner* — Eduardo C Robert
*Assistant Examiner* — Hao D Mai
(74) *Attorney, Agent, or Firm* — Fish & Richardson P.C.

(57) ABSTRACT

Implementations for obtaining objective measurements related to a patient's dental condition and reporting a patient's dental health based on these objective measurements are described herein. One or more of implementations can be used to provide an objective standard by which a patient's dental health can be evaluated. In some implementations, one or more numerical scores can be generated for a patient, where each score describes a different aspect of the patient's dental health. In some cases, a single dental health score can be generated to represent the patient's overall dental health. In some cases, dentists can use these implementations to improve the consistency and impartiality of their medical opinions, and to communicate more efficiently and effectively with others (e.g., other dentists, administrators, and patients).

35 Claims, 17 Drawing Sheets

(56) References Cited

U.S. PATENT DOCUMENTS

| | | | | |
|---|---|---|---|---|
| 2012/0116799 A1* | 5/2012 | Lindskog | ............... | G06F 19/345 |
| | | | | 705/2 |
| 2013/0122468 A1* | 5/2013 | Abrams | ................... | A61B 6/14 |
| | | | | 433/215 |
| 2015/0363567 A1* | 12/2015 | Pettus | ................. | G06F 19/3431 |
| | | | | 705/3 |
| 2016/0150995 A1* | 6/2016 | Ratto | ................... | A61B 5/0022 |
| | | | | 600/532 |
| 2016/0321806 A1* | 11/2016 | Gelbman | .............. | G06T 7/0012 |

* cited by examiner

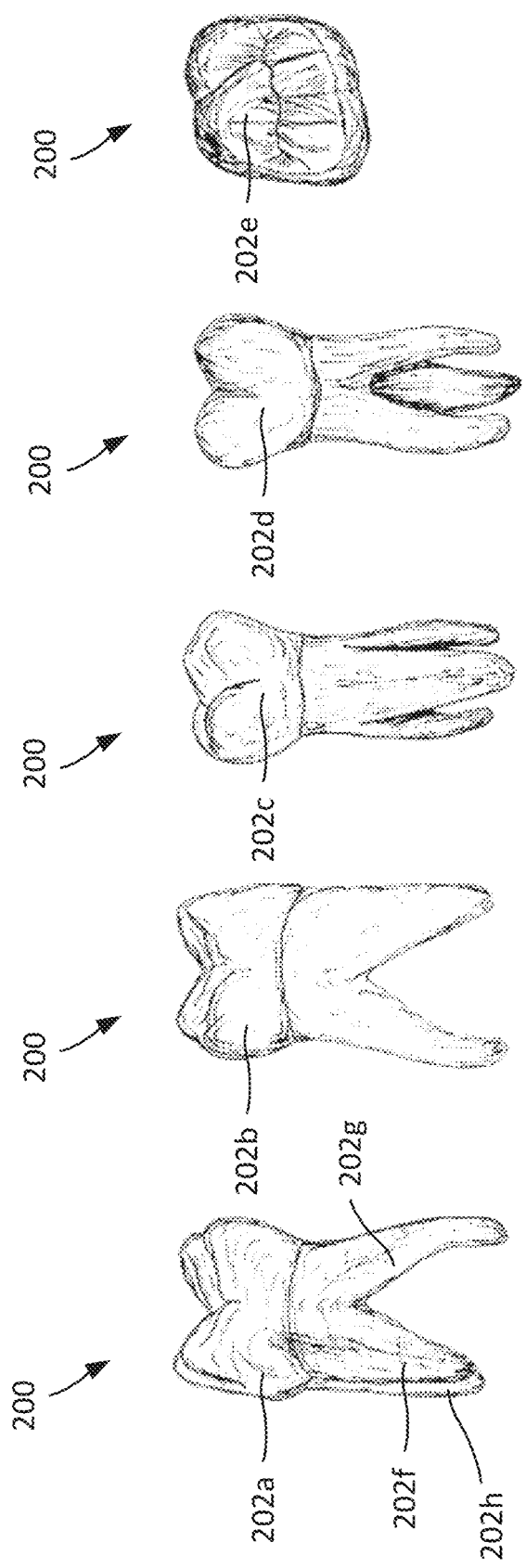

| First Aggregate Score (Hard Tissue Health) | Healthy | Gingivitis | Perio. – Early | Perio. – Mod. | Perio. – Adv. |
|---|---|---|---|---|---|
| Best | 11 | 12 | 13 | 14 | 15 |
| Good | 21 | 22 | 23 | 24 | 25 |
| Fair | 31 | 32 | 33 | 34 | 35 |
| Poor | 41 | 42 | 43 | 44 | 45 |

Second Aggregate Score (Periodontal Health)

FIG. 3

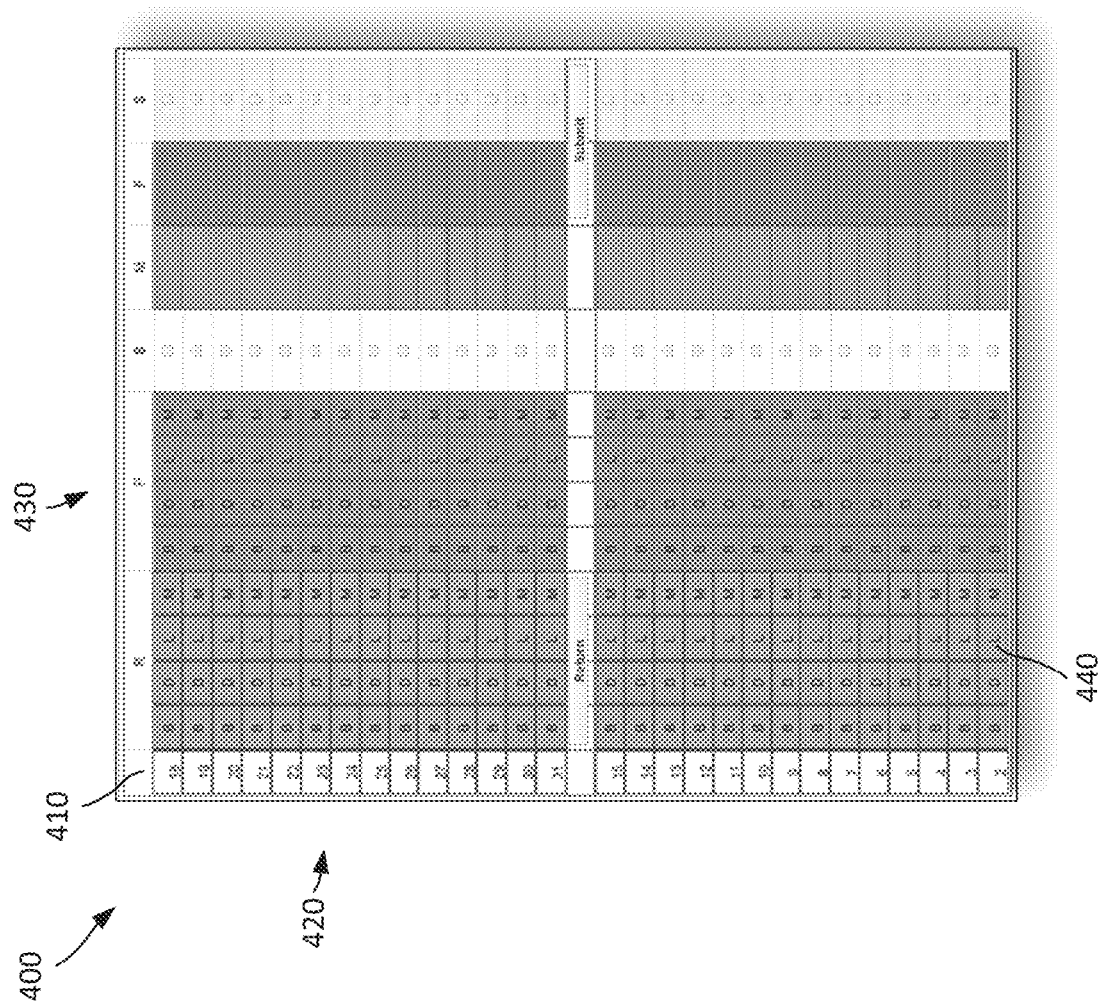

700

Dental Integra™
*Filling Your Dental Informatics Needs*

Visit Date January 24th, 2015

710a → Dear Joseph Patient,

We understand that your last medical examination on 01/01/2012 and that the Mount Kisco Medical Group is your medical health provider. You rate your medical health as being Good.

*From your intake form, you list that you have the following medical issues:*

710b → *Heart disease*
Your history of heart disease requires that you pre-medicate prior to all appointments that have a risk of incurring significant bacterial invasion of the bloodstream. This includes, and is not limited to oral surgery and routine dental cleanings. Since not every treatment involves the spread of bacteria, please confirm at the end of each treatment visit whether or not antibiotic coverage is necessary for the next visit. To reduce the oral bacterial count, your medical situation also would warrant the use of an antimicrobial mouth rinse, like chlorhexidine, to be used for one day prior to elective dental treatment.

*Diabetes*
Our experience, combined with your cooperation, should minimize the possibility of your diabetes complicating routine treatment; as long as the diabetes is well controlled. I would advise: 1. Eating normal meals before appointments. 2. Scheduling morning appointments. 3. Advising the doctor and staff of any symptoms when they first occur, 4. Having sugar in some form in case of insulin reaction. Should you develop an oral infection, you may require an increase in insulin dosage.

*Back problems*
We have been alerted to the fact that you have back problems. This is typically not a problem is the course of routine dental treatment. If you find that the dental chair does not afford the support that you back requires, please alert the doctor and staff. We will be more than happy to provide additional back support in order to make your treatment as comfortable as we can. When sitting up or lying back in the chair, we would suggest allowing the machinery of the equipment to raise and/or lower to the desired position, in order to minimize the strain to your back. The key to your comfort is open communication, just let us know what we can do to make your treatment comfortable.

710c → *Your report taking the following medications:*

*Clopidogrel*

*Coreg*
Carvedilol is a drug that can induce orthostatic hypotension primarily caused by gravity-induced blood pooling in the lower extremities. This compromises venous return, resulting in decreased cardiac output and subsequent lowering of arterial pressure. For example, changing from a lying position to standing loses about 700 ml of blood from the thorax, with a decrease in systolic and diastolic blood pressures. The overall effect is an insufficient blood perfusion in the upper part of the body resulting in symptoms like dizziness, headaches, and the like. On the completion of each visit, care should be taken not to stand too quickly. Instead, prior to walking, you should sit more upright for a moment to assess your potential for feeling lightheaded or dizzy.

*You have noted the following dental concerns:*

710d → *Tender or bleeding gums*
Your report of tender or bleeding gums is a very serious sign which could indicate that you may be experiencing problems with periodontal disease. Periodontal disease is a dental problem which is nearly a national epidemic, with probably 70% of the population being affected at sometime in their lives. The severity of periodontal disease varies greatly, ranging from acute reversible gingivitis to chronic refractory periodontitis- with inevitable tooth loss. In determining how best to eliminate your gum problems we will classify the stage of the disease process and recommend specific treatments. After active treatment maintence strategies will also be suggested. However, if your condition does not improve and the objective signs of the periodontal disease persist, you may require follow-up treatment with a periodontist.

*Sensitivity to cold*

FIG. 7A

710d (con't)

Cold sensitive teeth is a very common complaint today. Typically the number of teeth in your mouth that are sensitive is important to know. Generalized cold sensitivity, especially at the gumline- is often due to factors like freshly exposed root structure, abfracted enamel, and/or toothbrush abrasion. Patients who have undergone periodontal therapy will often experience a period of transient cold sensitivity due to the therapeutic removal of infected root covering. Fortunately, generalized root sensitivity usually responds to a variety of topical treatments, and/or simple bonding. When individual teeth experience cold sensitivity, problems may include decay and excessive bite forces, as well as exposed root structure, abfracted enamel, toothbrush abrasion, and teeth that may eventually need root canal therapy.

*Sensitivity to sweets*
If eating a chocolate bar no longer brings comfort, but rather a toothache, then chances are good that you have some kind of issue with decay. Sweet sensitivity is a very common problem and usually indicates a loss of some structure that protected the dentin or cementum of the tooth. Exposed dentin from a cavity, or exposed cementum on the root surface, could give you that sensation of nerve pain. Usually, as the sweets clear from your mouth, the discomfort subsides. Please note, however, that the degree of your discomfort is not necessarily proportional to your problem. Due to the all or none nature of the nervous system, even small cavities can cause tremendous pain. Conversely- we often see some very large cavities- some that even extend deeply into the nerve chamber that are totally pain-free. In combination with your report of symptoms, our clinical and x-ray examination have identified the source of your problem.

Radiographic examination:
The results of your full mouth x-rays series reveal the following findings:

Teeth number 6,9,23,28 show radiographic signs of new decay.

From past restorative intervention, tooth number 29 has had treatment for deep decay. The significance of this finding is that teeth which have had deep decay are more likely to have complications which may result in damage to the dental pulp. Depending on the extent of damage, these teeth might require some sort of future treatment, possibly root canal therapy, at worst- extraction. However, at this time there is no treatment required as the result of past disease to these teeth.

Numbers 4,7,10,20,30 have failed restorations and show evidence of secondary decay.

As a final finding on review of your films, I have noted that there is a 'foreign object' in the X quadrant /l area. This is incidental finding, the result of past dental treatment and simply for the sake of completeness has been brought to your attention. This finding requires no intervention and raises no concerns.

Tooth 3 reveals radiographic evidence of root resorption. This is an unusual finding which occasionally may be seen as the result of past trauma to the tooth. However, resorption is also often seen with no obvious precipitating event, in which case it is referred to as idiopathic. Unfortunately, along with this finding comes very, very guarded prognoses at best. More often than not, these teeth typically cannot be treated and/or retained.

A review of the periodontal ligament integrity reveals pathology of endodontic origin on teeth 4,19,20.

Examination of the periodontal ligaments of tooth 3 show what appear to be significant damage to the supporting socket due to periodontal disease.

Significantly decayed residual root tips are all that remain of teeth 3,9. As part of your treatment these remnants need to be removed.

*In addition to the radiographic examination, the use of Diagnodent laser cavity system reveals decay on the biting surfaces of teeth:*

4,5,13

Temporomandibular joint examination:
Damaged joint with dislocation and disk reduction.

The results of your Joint Vibration Analysis examination confirmed what we noted clinically. Your ability to open appears to be what would still be considered to be normal, but the joints articular disk position is out of alignment. Typically, this stage of dysfunction is characterized by the articular disk- the piece of cartilage interposed between the head of the mandibles condyle and the fossa of the skull, being somewhat dislocated from the top of the mandibles connection to the skull. This serious problem would be characterized as disk displacement with reduction, since the cartilage returns to its correct position during the course of opening. Normally, the articular disk offers both lubrication and protection against bone on bone contact in rest or function. When the condyle functions off the disk- but rather on the ligaments normally found behind the disk, there may or may not be adaption to this compromise. Our goal will be to maintain your range of motion without inducing pain: the possibility of more permanent disk recapture might be possible- but not likely given the degree of disk anatomy disruption and the time that has passed from when it was damaged. As with the taking of x-rays

710g for the monitoring of dental caries, JVA should be performed once a year to monitor for changes which may be detrimental to your joints health and your comfort.

Your Dental Integra Score is:

21

My examination of your mouth gives me cause for concern. Historically, you have enjoyed excellent soft tissue (periodontal) health. This can be seen by the fact that upon gentle probing your gums, which exhibit a healthy pink color and are tightly attached to the teeth and bone, do not exhibit any bleeding upon gentle probing. The pocket depth- the distance from the crest of the tissue to where it attaches to the tooth and bone is generally 3 millimeters or less in depth. This is considered good in that toothbrush bristles and floss can easily remove bacterial plaque from this area. In contrast, your dental (hard tissue) health, from second molar to second molar, appears to be a source of trouble. You have between 25 to 49 out of 196 tooth surfaces damaged or lost to disease. This means up to 25% of your tooth structure is in less than ideal condition. Damage to individual portions of a tooth's surfaces ultimately has a cumulative effect on that tooth's integrity and function. Even a single decayed tooth surface increases the likelihood of further damage to the tooth due to the inherent weakening of the tooth and the eventual maintenance that the restoration will require. The smaller the restoration, the less damage and potential for future complications. The larger the required restoration the greater the likelihood of needing more complex treatments like endodontic therapy, and in the worst case may eventually lead to tooth loss. Tooth loss may eventually lead to a compromise in the integrity of the dental arches that could have a significant affect on promoting further tooth loss or dysfunction.

Regards,

Panos Papapanou

FIG. 7C

SYSTEM AND METHOD FOR OBTAINING AN OBJECTIVE DENTAL HEALTH ANALYSIS

TECHNICAL FIELD

This disclosure relates to systems and methods for obtaining an objective dental health analysis.

BACKGROUND

When a patient seeks care from a dentist, the dentist will often conduct an examination to gain an understanding of the patient's overall dental health, as well as the patient's particular dental problems. While specific problems may be diagnosed, recorded, communicated (e.g., to the patient and/or others), and treated; the assessment of dental health is often subjective. For instance, several dentists may consider different aspects of the patient's dentition in rendering an opinion of the patient's dental health. Further, each can render an opinion based on different criteria. As a result, multiple dentists, in examining the same patient, may each render different opinions regarding that patient's dental health. In contrast, if these dentists evaluated the dental health of the patient using an objective standard, the consistency and impartiality of their medical opinions could improve. Such a standard could also allow them to communicate their opinions more efficiently and effectively with others.

SUMMARY

Implementations for obtaining objective measurements related to a patient's dental condition and reporting a patient's dental health based on these objective measurements are described below. One or more implementations can be used to provide an objective standard by which a patient's dental health can be evaluated. In some implementations, one or more numerical scores can be generated for a patient, where each score describes a different aspect of the patient's dental health. In some cases, a single dental health score can be generated to represent the patient's overall dental health. In some cases, dentists can use these implementations to improve the consistency and impartiality of their medical opinions, and to communicate more efficiently and effectively with others (e.g., other dentists, administrators, and patients).

In general, in an aspect, a method of assessing a patient's dental health includes receiving, at a processor, for each location of a plurality of tooth locations, a corresponding first set of data and a corresponding second set of data. The first set of data indicates a physical condition of a tooth at the location, and the second set of data indicates at least one physical parameter of the tooth at the location. The method also includes determining, by the processor, for each location of the plurality of tooth locations, a first score based on the corresponding first set of data, where the first score indicates a hard tissue health of a tooth at the location. The method also includes determining, by the processor, a first aggregate score based on at least one or more of the first scores, where the first aggregate score indicates a hard tissue health of the patient. The method also includes determining, by the processor, for each location of the plurality of tooth locations, a second score based on the corresponding second set of data. The second score indicates a periodontal health associated with a tooth at the location. The method also includes determining, by the processor, a second aggregate score based at least in part on one or more of the second scores, where the second aggregate score indicates a periodontal health of the patient. The method also includes determining, by the processor, a dental health score based on the first aggregate score and the second aggregate score, where the dental health score indicates an overall dental health of the patient. The method also includes outputting the dental health score to a display device.

In general, in another aspect, a non-transitory computer-readable medium includes instructions which, when executed by one or more processors causes receiving, at a processor, for each location of a plurality of tooth locations, a corresponding first set of data and a corresponding second set of data. The first set of data indicates a physical condition of a tooth at the location, and the second set of data indicates at least one physical parameter of the tooth at the location. The instructions, when executed, also causes determining, by the processor, for each location of the plurality of tooth locations, a first score based on the corresponding first set of data, where the first score indicates a hard tissue health of a tooth at the location. The instructions, when executed, also causes determining, by the processor, a first aggregate score based on at least one or more of the first scores, where the first aggregate score indicates a hard tissue health of the patient. The instructions, when executed, also causes determining, by the processor, for each location of the plurality of tooth locations, a second score based on the corresponding second set of data. The second score indicates a periodontal health associated with a tooth at the location. The instructions, when executed, also causes determining, by the processor, a second aggregate score based at least in part on one or more of the second scores, where the second aggregate score indicates a periodontal health of the patient. The instructions, when executed, also causes determining, by the processor, a dental health score based on the first aggregate score and the second aggregate score, where the dental health score indicates an overall dental health of the patient. The instructions, when executed, also causes outputting the dental health score to a display device.

Implementations of these aspects may include one or more of the following features.

In some implementations, each first set of data can include a parameter specifying a number of surfaces of the tooth at the corresponding location that are damaged or missing. Determination of each first score can be based on the number of surfaces of the tooth at the corresponding location that are damaged or missing.

In some implementations, determining the first aggregate score can include summing, by the processor, the first scores, selecting, by the processor, a particular hard tissue health category from among a plurality of hard tissue health categories based on the sum of the first scores, and determining, by the processor, the first aggregate score based on the selected hard tissue health category. Each second set of data can include an average crown length of the tooth at the corresponding location, an average root length of the tooth at the corresponding location, a gingival attachment length of the tooth at the corresponding location, a root tip length of the tooth at the corresponding location, and a combined attachment loss of the tooth at the corresponding location.

In some implementations, determining each second score can further include receiving, at the processor, an indication that the tooth at the corresponding location exhibits bleeding upon probing, and upon receiving the indication that the tooth at the corresponding location exhibits bleeding upon probing, modifying the second score by the processor, wherein modifying the second score comprises reducing the second score by a pre-determined value.

In some implementations, determining each second score can further include receiving, at the processor, an indication that the tooth at the corresponding location exhibits suppuration, and upon receiving the indication that the tooth at the corresponding location exhibits suppuration, modifying the second score by the processor. Modifying the second score can include reducing the second score by a pre-determined value.

In some implementations, determining each second score can further include receiving, at the processor, an indication of a degree of mobility of the tooth at the corresponding location, and upon receiving the indication of the degree of mobility of the tooth at the corresponding location, modifying the second score by the processor. Modifying the second score can include reducing the second score by a pre-determined value.

In some implementations, determining each second score can further include receiving, at the processor, an indication of a degree of furcation involvement of the tooth at the corresponding location, and upon receiving the indication of the degree of furcation involvement of the tooth at the corresponding location, modifying the second score by the processor. Modifying the second score can include reducing the second score by a pre-determined value.

In some implementations, determining each second score can further include receiving, at the processor, an indication of a root to crown ratio of the tooth at the corresponding location, and upon receiving the indication of the root to crown ratio of the tooth at the corresponding location, determining a modifier score based on the root to crown ratio of the tooth at the corresponding location and modifying the second score by the processor. Modifying the second score can include reducing the second score by the modifier score.

In some implementations, determining the second aggregate score can include determining, by the processor, an average of the second scores for each region of a plurality of regions of a patient's mouth, where each average of the second scores corresponds to teeth of a different respective region, selecting, by the processor, a particular periodontal health category from among a plurality of periodontal health categories based on the averages of the second scores, and determining, by the processor, the second aggregate score based on the selected periodontal health category.

In some implementations, determining the dental health score can include adding, by the processor, the first aggregate score and the second aggregate score.

In some implementations, the method can further include determining, by the processor, a course of treatment for the patient based at least in part on the dental health score. The method can further include outputting to a display the determined course of treatment as a recommended course of treatment.

In some implementations, the instructions, when executed, can further cause determining, by the processor, a course of treatment for the patient based at least in part on the dental health score. The instructions, when executed, can further cause outputting to a display the determined course of treatment as a recommended course of treatment In some implementations, the method can further include automatically generating, by the processor, a narrative describing the dental health of the patient based on the dental health score, and outputting the narrative to a display device. Automatically generating the narrative can include obtaining, by the processor, a plurality of narrative templates, each corresponding to a different dental health condition, and automatically selecting, by the processor, at least one of the narrative templates based on the dental health score.

In some implementations, the instructions, when executed, can further cause automatically generating, by the processor, a narrative describing the dental health of the patient based on the dental health score, and outputting the narrative to a display device. Automatically generating the narrative can include obtaining, by the processor, a plurality of narrative templates, each corresponding to a different dental health condition, and automatically selecting, by the processor, at least one of the narrative templates based on the dental health score.

The details of one or more embodiments are set forth in the accompanying drawings and the description below. Other features and advantages will be apparent from the description, drawings, and the claims.

DESCRIPTION OF DRAWINGS

FIGS. 2A-D are diagrams illustrating four sides of an example tooth.

FIG. 2E is a diagram illustrating the top of the example tooth shown in FIGS. 2A-D.

FIG. 3 is a table illustrating an example of a relationship between a first aggregate score, a second aggregate score, and a dental health score.

FIGS. 4A and 4B are screen shots illustrating examples of user interfaces for inputting data.

FIGS. 7A-C illustrate an example narrative that is generated based on a determined dental health score.

DETAILED DESCRIPTION

Implementations for obtaining objective measurements related to a patient's dental condition, and reporting a patient's dental health based on the objective measurements are described herein. One or more of implementations can be used to provide an objective standard by which a patient's dental health can be evaluated. In some cases, dentists can use this standard to improve the consistency and impartiality of their medical opinions, and can use the results of this standard to more efficiently and effectively communicate with others (e.g., other dentists, administrators, and patients).

Figure 1:
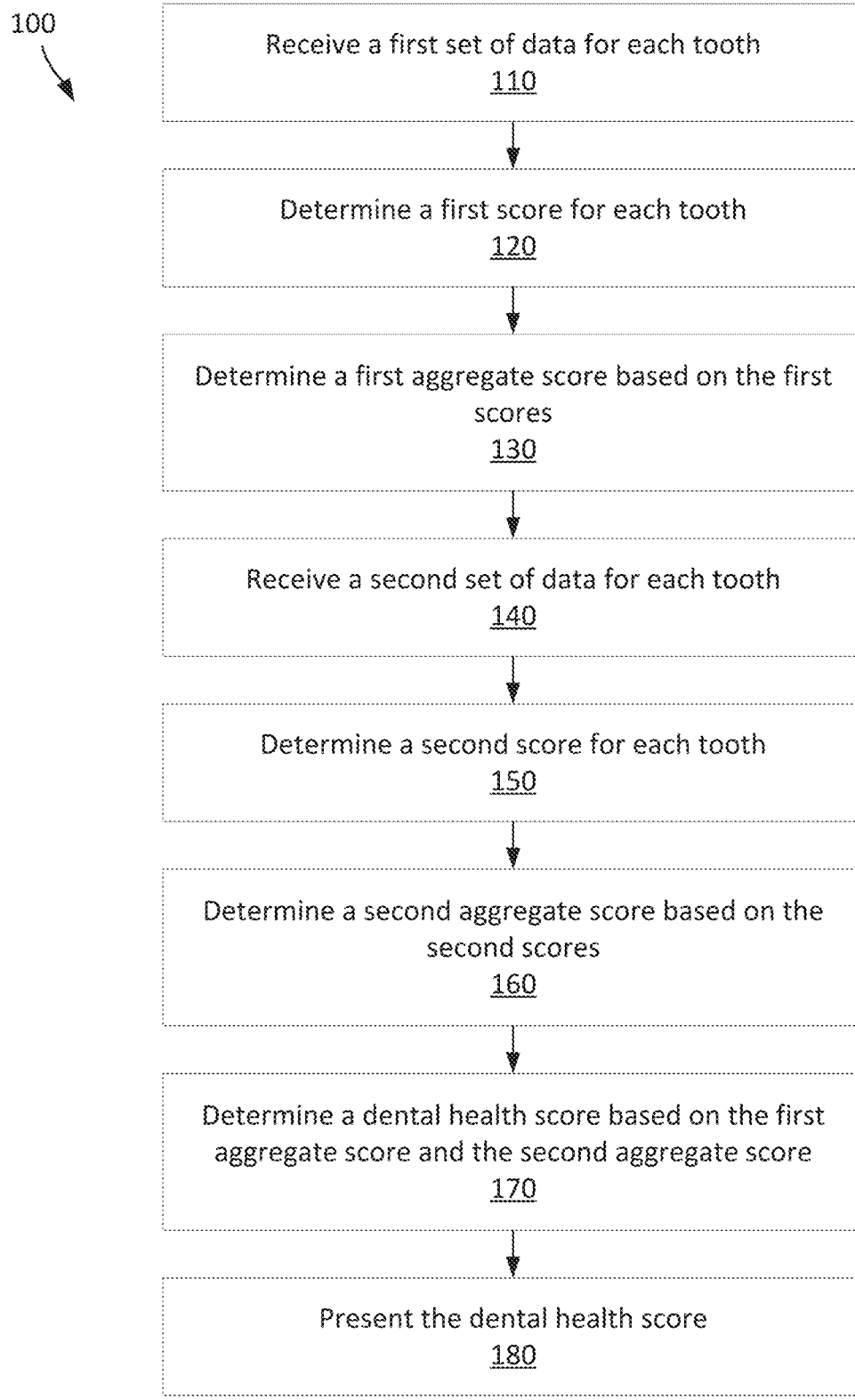
FIG. 1 is a flow chart of an example process for assessing a patient's dental health.

An example process 100 for assessing a patient's dental health is shown in FIG. 1.

The process 100 begins by receiving a first set of data for each of a patient's teeth (step 110). These first sets of data can be used to evaluate the hard tissue health of each tooth. The hard tissue of a tooth can include, for example, the enamel, dentin, and cementum of the tooth.

In some cases, each first set of data specifies, among other things, a number of surfaces of a corresponding tooth that are damaged or missing. For example, for a given tooth, a first set of data can include a parameter value that indicates the number of surfaces of that tooth that are damaged (e.g., due to poor dental hygiene or trauma) and/or missing (e.g., removed as a result of trauma or a surgical procedure) relative to a healthy, undamaged, or otherwise normal version of that tooth (e.g., a "virgin" tooth). In some implementations, anatomical aspects of the tooth can be described as "surfaces." The definition of each surface can be standardized, such that the first set of data provides consistent and objective information. In some cases, the total number of surfaces for each tooth can also be standardized to a common value, even if different teeth may normally have different numbers of surfaces. For example, in some cases, each tooth can be assumed to have seven total surfaces: five surfaces for the anatomical crown of the tooth (e.g., a buccal surface, a distal surface, a lingual surface, a mesial surface, and an occlusal surface), and two for the roots of the tooth. If a tooth is missing (e.g., completely absent from the patient), the parameter value for that tooth can indicate that all of the assumed surfaces (e.g., all seven surfaces) are missing.

In some cases, the parameter value for a tooth can also reflect repairs that have been made to that tooth. For example, if a single surface of a patient's tooth has been damaged, the parameter value might indicate that one surface is damaged. However, if that surface is later repaired (e.g., through a dental procedure), the parameter value might indicate that none of the surfaces of that tooth are damaged. Thus, the parameter value can be used to indicate the current physical condition of the tooth, taking in account repairs and corrective actions that have been performed on that tooth.

In some cases, only specific kinds of repairs made to certain portions of a tooth can affect the parameter value in this way, while repairs of a different nature do not affect the parameter value. For instance, in some implementations, only repairs made to the crown of the tooth (e.g., the clinical crown) with highly durable materials (e.g., full cast metal crown repair, or an implant having a replacement crown) will be reflected in the parameter value, while repairs made with less durable materials (e.g., dental amalgam or composite fillings) will not be reflected in the parameter value. This can be useful in some circumstances, as certain types of repairs (e.g., repairs performed using less durable materials) may stop or otherwise reduce the disease process of a tooth, but may not sufficiently address the greater risk for additional damage that can result from the repair itself (e.g., tooth fracture and other possible consequences). In contrast, certain other types of repairs (e.g., repairs performed using more durable materials) may stop or otherwise reduce the disease process of the tooth, and also reduce the risk for additional damage. Thus, in some circumstances, the parameter value can be determined based, at least in part, on the type of repair being made.

In some cases, a first set of data can be collected for each and every one of a patient's teeth. For example, a parameter value can be obtained for each of a patient's teeth in order to indicate each and every damaged or missing surface of the patient's teeth. In practice, however, a first set of data can be collected for each tooth of a subset of a patient's teeth. For example, in some cases, a first set of data can be collected for a single tooth, or multiple teeth (e.g., two, three, four, five, and so forth). In some cases, a first set of data can be collected for each tooth from a particular region (e.g., a particular quadrant or sextant to the patient's mouth). In some case, parameter values can be obtained for a standardized number of teeth. For example, in some implementations, a parameter value can be obtained for each of twenty eight teeth (e.g., the number of teeth of a normal, healthy human, excluding wisdom teeth). As another example, in some implementations, a parameter value can also be obtained for each of twenty four teeth (e.g., the number of teeth of a normal, healthy human, excluding wisdom teeth and teeth removed for orthodontic therapy). Other standardized numbers of teeth can also be used, depending on the implementation.

The first sets of data can be received from one or more different sources. For example, in some cases, one or more first sets of data can be received from an electronic database (e.g., an electronic database maintained on a single computer system, or distributively maintained across several interconnected computer systems, such as a "cloud" computer system). The contents of these electronic databases can be based on user input (e.g., based on observations made by a dentist), and/or based determinations made by one or more computer systems (e.g., based on analyses conducted by a computer system on one or more data sets). In some cases, all or part of an electronic database can be retrieved from a computer system using an application programming interface (API), which defines what types of information can be retrieved from a particular electronic database, and how the information can be retrieved. In some cases, one or more first sets of data can be received directly from one or more users (e.g., input obtained from a user interacting with the user interface of a computer system).

After receiving a first set of data for each tooth, the process 100 continues by determining a first score for each tooth based on the first sets of data (step 120). As described herein, in some cases, each first set of data can include a parameter value that indicates the number of surfaces the tooth that are damaged and/or missing relative to a healthy version of that tooth (e.g., a "virgin" or undamaged tooth). In these cases, a first score can be determined for each tooth by subtracting the number of damaged and/or missing surfaces from the assumed total number of surfaces.

As an example, some implementations assume that each tooth, when healthy, has a total of seven surfaces. Thus, if the first set of data indicates that one surface is damaged (e.g., one surface of the clinical crown), the first score is determined to be six (i.e., seven minus one). As another example, if the first set of data indicates that two surfaces of the crown are damaged, the first score is determined to be five (i.e., seven minus two). As another example, if the first set of data indicates that one surface of the clinical crown is damaged but was subsequently repaired (e.g., with a cast metal crown), the first score is determined to be seven.

In some cases, the first score can depend on whether the damage is to the crown or the root. For instance, in some cases, damage to a root can result in a first score of zero for that tooth. This can be useful, for example, as the presence of the crown is dependent on the presence of a root system. As an example, if the first set of data indicates that the roots are missing, the first score is determined to be zero. As another example, if the first set of data indicates that a root surface is totally damaged but was subsequently repaired (e.g. by implant restoration), the first score is determined to be two (e.g., the two roots). If all surfaces of that tooth's crown are subsequently repaired, the first score is determined to be seven.

As noted herein, in some cases, the total number of surfaces of each tooth can be standardized, even if different teeth may normally have different numbers of surfaces. In these cases, only a number of surfaces of that tooth that are damaged and/or missing relative to the healthy version of that tooth are subtracted from the assumed total. As an example, in some cases, a healthy tooth might have six surfaces (e.g., five surfaces for the crown, and a single root surface), but may be standardized to have an assumed total of seven surfaces (e.g., five surfaces for the crown, and two roots surfaces). In this case, damage to a single crown surface would result in a first score of six (i.e., seven minus one), even though the tooth, when healthy, anatomically has six surfaces. As another example, in some cases, a healthy tooth might have eight surfaces (e.g., five surfaces for the crown, and three root surfaces), but may be standardized to have an assumed total of seven surfaces (e.g., five surfaces for the crown, and two root surfaces). In this case, damage to a single crown surface would result in a first score of six (i.e., seven minus one), even though the tooth, when healthy, anatomically has eight surfaces. As noted herein, however, if a tooth is missing (e.g., completely absent from the patient), the parameter value for that tooth can indicate that all of the assumed surfaces (e.g., all seven surfaces) are missing. As an example, a tooth normally having eight surfaces might be standardized to have an assumed total of seven surfaces; if that tooth is missing, the parameter value for the tooth can indicate that all of the assumed surfaces (e.g., all seven surfaces) are missing, resulting in a first score of zero. In this manner, in some cases, the first scores can be locked within a particular range (e.g., zero to seven), regardless of the number of surfaces that the tooth might have anatomically (e.g., due to a varying number of roots).

As an example, FIGS. 2A-D show a side view from each of four different sides of a tooth 200, and FIG. 2E shows a top view of the tooth 200. Each of eight surfaces 202a-h are indicated in FIGS. 2A-E. In this example, the tooth 200 has three roots, where each root corresponds to a different respective surface 202f-h. As discussed herein, in some cases, the number of surfaces can be standardized to a particular number. For example, even though the tooth 200 has eight surfaces 202a-h, it can be standardized to have seven surfaces (e.g., five surfaces and two root surfaces).

After determining a first score for each tooth, the process 100 continues by determining a first aggregate score based on the first scores (step 130). In some implementations, the first aggregate score can be determined by first adding each of the individual first scores together. As noted herein, in some cases, each tooth is assumed to have a total of seven surfaces (when healthy), and 28 total teeth are considered. Thus, in this case, the patient can have a maximum sum of 196, assuming every tooth is healthy. However, depending on the physical condition of the patient's teeth (e.g., if one or more teeth have damaged or missing surfaces), the sum can be as low as zero (e.g., indicating that the patient has no teeth). Although a first aggregate score can be determined based on multiple first scores, in some case, a first aggregate score can be determined based on a single first score (e.g., a first score for a single tooth).

After the sum of the first scores is calculated, the sum can be used to select one of several possible hard tissue health categories, where each category indicates a different hard tissue health state of the patient. As an example, in some cases, the categories can include a "best" category (e.g., indicating a relatively low degree of hard tissue damage), a "good" category (e.g., indicating a relatively greater degree of hard tissue damage), a "fair" category (e.g., indicating an even greater degree of hard tissue damage), and a "poor" category (e.g., indicating an even greater degree of hard tissue damage still). In some cases, each category can be defined according to a range of potential sums. Thus, based on the determined sum, a particular category can be selected. As an example, in some cases, a "best" category can be defined by sums indicating approximately 0-15% damage (e.g., sums between approximately 166-196), a "good" category can be defined by sums indicating greater than approximately 15% damage but less than or equal to than approximately 25% damage (e.g., sums between approximately 147-165), a "fair" category can be defined by sums indicating greater than approximately 25% damage but less than or equal to 50% (e.g., sums between approximately 98-146), and a "poor" category can be defined by sums indicating approximately greater than approximately 50% damage (e.g., sums between approximately 0-97).

Once a category has been selected, the selected category can be used to determine the first aggregate score. In some cases, each category is assigned a particular value (e.g., 10 for "best," 20 for "good," 30 for "fair," and 40 for "poor"). This value can be used as the first aggregate score. As an example, a patient having no damage to his teeth (e.g., having a sum of first scores of 196) has a corresponding first aggregate score of 10. As another example, a patient having approximately 20% damage (e.g., having a sum of approximately 157) has a corresponding first aggregate score of 20.

Although example categories (and corresponding ranges of sums and first aggregate scores) are described herein, these are merely illustrative examples. In practice, other categories (e.g., a greater number or a fewer number of categories) can be used, depending on the implementation. Likewise, each range of sums and each first aggregate score can also differ, depending on the application. Further, although the categories described herein are described as "best," "good," "fair," and "poor," these are merely example labels that can be used to describe each category. In practice, other labels can be used, depending on the implementation. Further, in some cases, one or more teeth can be excluded, such that data is not collected for these teeth and/or such that the condition of those teeth does not affect the calculation of the first aggregate score.

After determining a first aggregate score, the process 100 continues by receiving a second set of data for each tooth (step 140). These second sets of data can be used to evaluate the periodontal health of each tooth.

Figure 2F:
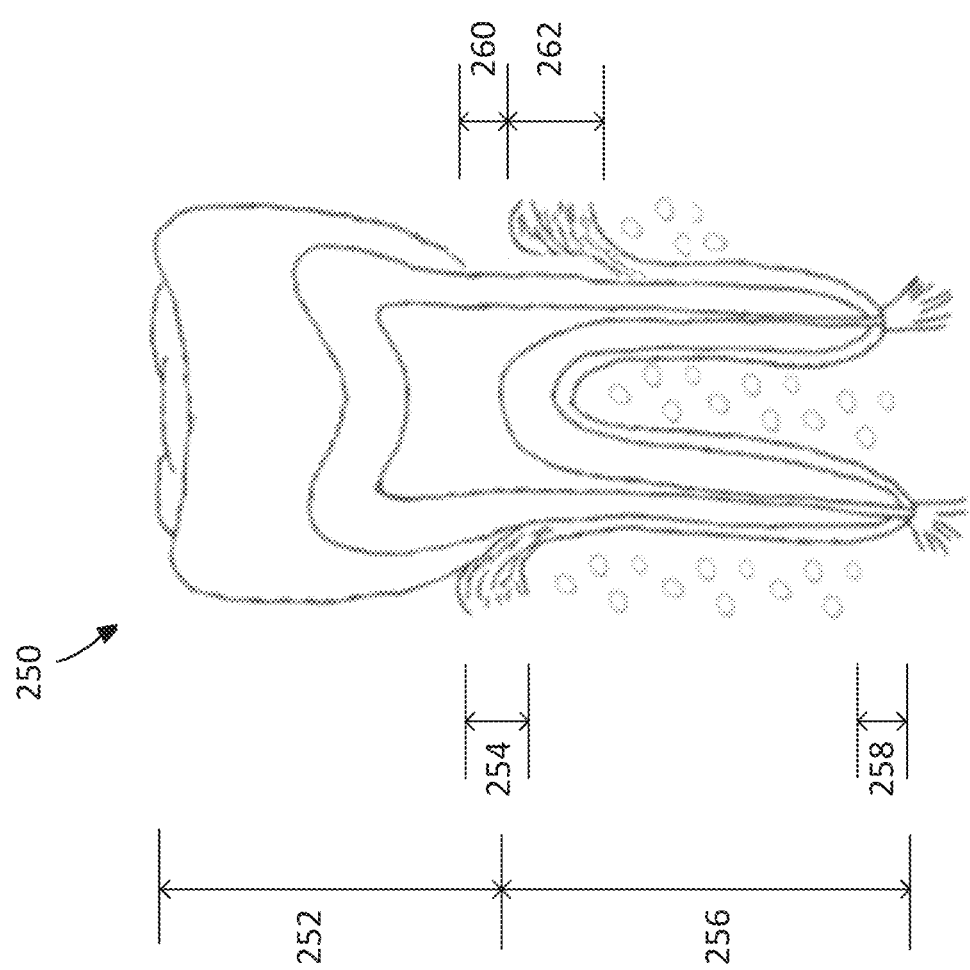
FIG. 2F is a schematic that shows a cross-sectional view of another example tooth.

In some cases, each second set of data specifies, among other things, particular physical characteristics of the tooth and the surrounding tissue, such the tooth's physical dimensions, the dimensions of the soft tissue surrounding the tooth, or the state of the soft tissue surrounding the tooth. For instance, each second set of data can include parameter values that specify one or more crown lengths of the tooth (e.g., the length of the anatomical crown), one or more a gingival attachment lengths of the tooth, one or more root lengths of the tooth (e.g., the anatomical root), and one or more root tip lengths of the tooth. As an example, FIG. 2F shows a cross-sectional view of an example tooth 250. The crown length 252, the gingival attachment length 254, the root length 256, and the root tip length 258 of the tooth 250 are indicated in FIG. 2F. Each second set of data can also include additional information, such as data regarding the recession of the tooth and the pocket depth of the tooth. As examples, the recession 260 and the pocket depth 262 of the tooth 250 are also indicated in FIG. 2F.

In some cases, each second set of data can include multiple measurements taken from each of several different sides of the tooth. For example, in some cases, each second set of data can include parameter values that specify the anatomical crown length of the tooth along each of the tooth's buccal, distal, lingual, and mesial sides. Similarly, each second set of data can also include parameter values that specify the tooth's gingival attachment lengths, root lengths, root tip lengths, recession, and pocket depth along each of these different sides.

In some cases, a second set of data can be collected for each and every one of a patient's teeth. In practice, however, a second set of data can be collected for each tooth of a subset of a patient's teeth. For example, in some cases, a first set of data can be collected for a single tooth, or multiple teeth (e.g., two, three, four, five, and so forth). In some cases, a first set of data can be collected for each tooth from a particular region (e.g., a particular quadrant or sextant to the patient's mouth). In some case, parameter values can be obtained for a standardized number of teeth. For example, in some implementations, a parameter value can be obtained for each of twenty eight teeth (e.g., the number of teeth of a normal, healthy human, excluding wisdom teeth). As another example, in some implementations, a parameter value can also be obtained for each of twenty four teeth (e.g., the number of teeth of a normal, healthy human, excluding wisdom teeth and teeth removed for orthodontic therapy). Other standardized numbers of teeth can also be used, depending on the implementation.

The second sets of data can be received from one or more different sources. For example, in some cases, one or more second sets of data can be received from an electronic database (e.g., an electronic database maintained on a single computer system, or distributively maintained across several interconnected computer systems, such as a "cloud" computer system). The contents of these electronic databases can be based on user input (e.g., based on observations made by a dentist), and/or based determinations made by one or more computer systems (e.g., based on analyses conducted by a computer system on one or more data sets). In some cases, all or part of an electronic database can be retrieved from a computer system using an application programming interface (API), which defines what types of information can be retrieved from a particular electronic database, and how the information can be retrieved. In some cases, one or more second sets of data can be received directly from one or more users (e.g., input obtained from a user interacting with the user interface of a computer system).

After receiving a second set of data for each tooth, the process 100 continues by determining a second score for each tooth (step 150). The second score for each tooth can be based, at least in part, on the second set of data corresponding to that tooth.

Various intermediate parameters can be used to determine each second score. As an example, in some cases, an effective root length (ERL) parameter can be calculated using the following relationship:

ERL=(ARL−RTL)−(R+PD), where ARL is the average root length (e.g., the root length 256), RTL is the root tip length (e.g., the root tip length 258), R is the recession (e.g., the recession 260), and PD is the pocket depth (e.g., the pocket depth 262). These values can be defined in various units of measurement, such as in millimeters.

In some implementations, one or more values can be determined based on direct observations of the patient (e.g., based on individual measurements obtained for that particular patient). In some implementations, one or more of the values can be estimates based wholly or partially on direct observations of the patient.

In some implementations, one or more of the values can be estimates based wholly or partially on observations of people other than the patient at hand. For example, in some cases, the average root length (ARL) need not correspond specifically to the patient's tooth, but rather to an average root length of a particular population of patients (e.g., a general population of patients, or a specific population of patients having particular characteristics similar to that of the patient at hand). In some implementations, one or more of values can be determined using a standardized table of values, such that individual measurements of that patient are not needed to determine those particular values. For instance, in some cases, the average root length (ARL) can be determined using a table of root length values, where each value indicates an average root length (ARL) for a general population of patients. This table can be determined, for example, based on values found in reference publications commonly used in dental practice. As an example, an average root length (ARL) table is shown in Table 1.

TABLE 1

Example average root length (ARL) reference table (values in mm).

| Tooth Location | Buccal Side | Distal Side | Lingual Side | Mesial Side |
|---|---|---|---|---|
| 1 | 11.0 | 11.0 | 11.0 | 11.0 |
| 2 | 11.0 | 11.0 | 11.0 | 11.0 |
| 3 | 12.0 | 12.0 | 12.0 | 12.0 |
| 4 | 14.0 | 14.0 | 14.0 | 14.0 |
| 5 | 14.0 | 14.0 | 14.0 | 14.0 |
| 6 | 17.0 | 17.0 | 17.0 | 17.0 |
| 7 | 13.0 | 13.0 | 13.0 | 13.0 |
| 8 | 13.0 | 13.0 | 13.0 | 13.0 |
| 9 | 13.0 | 13.0 | 13.0 | 13.0 |
| 10 | 13.0 | 13.0 | 13.0 | 13.0 |
| 11 | 17.0 | 17.0 | 17.0 | 17.0 |
| 12 | 14.0 | 14.0 | 14.0 | 14.0 |
| 13 | 14.0 | 14.0 | 14.0 | 14.0 |
| 14 | 12.0 | 12.0 | 12.0 | 12.0 |
| 15 | 11.0 | 11.0 | 11.0 | 11.0 |
| 16 | 11.0 | 11.0 | 11.0 | 11.0 |
| 17 | 11.0 | 11.0 | 11.0 | 11.0 |
| 18 | 13.0 | 13.0 | 13.0 | 13.0 |
| 19 | 14.0 | 14.0 | 14.0 | 14.0 |
| 20 | 14.5 | 14.5 | 14.5 | 14.5 |
| 21 | 14.0 | 14.0 | 14.0 | 14.0 |
| 22 | 16.0 | 16.0 | 16.0 | 16.0 |
| 23 | 14.0 | 14.0 | 14.0 | 14.0 |
| 24 | 12.5 | 12.5 | 12.5 | 12.5 |
| 25 | 12.5 | 12.5 | 12.5 | 12.5 |
| 26 | 14.0 | 14.0 | 14.0 | 14.0 |
| 27 | 16.0 | 16.0 | 16.0 | 16.0 |
| 28 | 14.0 | 14.0 | 14.0 | 14.0 |
| 29 | 14.5 | 14.5 | 14.5 | 14.5 |
| 30 | 14.0 | 14.0 | 14.0 | 14.0 |
| 31 | 13.0 | 13.0 | 13.0 | 13.0 |
| 32 | 11.0 | 11.0 | 11.0 | 11.0 |

Thus, in some cases, the average root length (ARL) for a given surface of a tooth can be determined by finding the corresponding tooth location and side from the average root length (ARL) table, and using the value listed.

Although an example of average root length (ARL) table is shown in Table 1, this is merely an illustrative example. In practice, other tables having similar or different can be used, depending on the implementation.

A net root support (NRS) parameter can be calculated using the following relationship:

NRS=ERL−GAL, where GAL is the gingival attachment length (e.g., the gingival attachment length 254). These values can be defined in various units of measurement, such as in millimeters.

A bone support (BS) parameter can be calculated using the following relationship:

BS=ARL−(RTL+GAL).

As noted herein, in some implementations, one or more of these values can be determined using a standardized table of values, such that individual measurements of that patient are not needed to determine those particular values. For instance, in some cases, the average root length (ARL) can be determined using a table of root length values, where each value indicates an average root length (ARL) for a general population of patients (e.g., as shown in Table 1).

An effective crown length (ECL) parameter can be calculated using the following relationship:

ECL=(ERL−NRS)+(ACL+R+PD), where ACL is the average crown length (e.g., the crown length 252). These values can be defined in various units of measurement, such as in millimeters.

As noted herein, in some implementations, one or more of the values can be estimates based wholly or partially on observations of people other than the patient at hand. For example, in some cases, the average crown length (ACL) need not correspond specifically to the patient's tooth, but rather to an average crown length of a particular population of patients (e.g., a general population of patients, or a specific population of patients having particular characteristics similar to that of the patient at hand). As noted herein, in some implementations, one or more of values can be determined using a standardized table of values, such that individual measurements of that patient are not needed to determine those particular values. For instance, in some cases, the average crown length (ACL) can be determined using a table of crown length values, where each value indicates an average crown length (ACL) for a general population of patients. This table can be determined, for example, based on values found in reference publications commonly used in dental practice. As an example, an average crown length (ACL) table is shown in Table 2.

TABLE 2

Example average crown length (ACL) reference table (values in mm).

| Tooth Location | Buccal Side | Distal Side | Lingual Side | Mesial Side |
|---|---|---|---|---|
| 1 | 6.5 | 6.5 | 6.5 | 6.5 |
| 2 | 7.0 | 7.0 | 7.0 | 7.0 |
| 3 | 7.5 | 7.5 | 7.5 | 7.5 |
| 4 | 8.5 | 8.5 | 8.5 | 8.5 |
| 5 | 8.5 | 8.5 | 8.5 | 8.5 |
| 6 | 10.0 | 10.0 | 10.0 | 10.0 |
| 7 | 9.0 | 9.0 | 9.0 | 9.0 |
| 8 | 10.5 | 10.5 | 10.5 | 10.5 |
| 9 | 10.5 | 10.5 | 10.5 | 10.5 |
| 10 | 9.0 | 9.0 | 9.0 | 9.0 |
| 11 | 10.0 | 10.0 | 10.0 | 10.0 |
| 12 | 8.5 | 8.5 | 8.5 | 8.5 |
| 13 | 8.5 | 8.5 | 8.5 | 8.5 |
| 14 | 7.5 | 7.5 | 7.5 | 7.5 |
| 15 | 7.0 | 7.0 | 7.0 | 7.0 |
| 16 | 6.5 | 6.5 | 6.5 | 6.5 |
| 17 | 7.0 | 7.0 | 7.0 | 7.0 |
| 18 | 7.0 | 7.0 | 7.0 | 7.0 |
| 19 | 7.5 | 7.5 | 7.5 | 7.5 |
| 20 | 8.0 | 8.0 | 8.0 | 8.0 |
| 21 | 8.5 | 8.5 | 8.5 | 8.5 |
| 22 | 11.0 | 11.0 | 11.0 | 11.0 |
| 23 | 9.5 | 9.5 | 9.5 | 9.5 |
| 24 | 9.0 | 9.0 | 9.0 | 9.0 |
| 25 | 9.0 | 9.0 | 9.0 | 9.0 |
| 26 | 9.5 | 9.5 | 9.5 | 9.5 |
| 27 | 11.0 | 11.0 | 11.0 | 11.0 |
| 28 | 8.5 | 8.5 | 8.5 | 8.5 |
| 29 | 8.0 | 8.0 | 8.0 | 8.0 |
| 30 | 7.5 | 7.5 | 7.5 | 7.5 |
| 31 | 7.0 | 7.0 | 7.0 | 7.0 |
| 32 | 7.0 | 7.0 | 7.0 | 7.0 |

Thus, in some cases, the average crown length (ACL) for a given surface of a tooth can be determined by finding the corresponding tooth location and side from the average crown length (ACL) table, and using the value listed.

Although an example of average crown length (ACL) table is shown in Table 2, this is merely an illustrative example. In practice, other tables having similar or different can be used, depending on the implementation.

An effective root percentage (ERP) parameter can be calculated using the following relationship:

$$ERP = \frac{NRS}{BS} \ (\%).$$

As noted herein, in some cases, each second set of data can include multiple measurements taken from each of several different sides of the tooth (e.g., individual measurements for the buccal, distal, lingual, and mesial side of each tooth). In these cases, an effective root percentage (ERP) can be individually calculated for each side of a tooth. The resulting effective root percentage parameters are then averaged together to obtain the overall effective root percentage (oERP) of the tooth.

Based on a tooth's overall effective root percentage (oERP), a second score is calculated for each tooth. In some cases, each tooth's overall effective root percentage (oERP) is used to select one of several possible categories, where each category indicates a different periodontal health state of the tooth. In some cases, each category can be defined according to a range of potential overall effective root percentage (oERP) values. Thus, based on the determined overall effective root percentage (oERP), a particular category can be selected. As an example, in some cases, a first category (indicating relatively high periodontal health) can be defined by an oERP of greater than or equal to approximately 67%, a second category (indicating relatively lower periodontal health) can be defined by an oERP of greater than or equal to approximately 56% and less than 67%, a third category (indicating even lower periodontal health) can be defined by an oERP of greater than or equal to approximately 44% and less than 56%, and a fourth category (indicating even lower periodontal health still) category can be defined by an oERP of less than approximately 44%.

Once a category has been selected for each tooth, the selected category can be used to determine the second score for the tooth. In some cases, each category is assigned a particular value (e.g., 40 for the first category, 30 for the second category, 20 for the third category, and 10 for the fourth category). As an example, a tooth having an overall effective root percentage (oERP) of 70% has a corresponding second score of 40. As an example, a tooth having an overall effective root percentage (oERP) of 50% has a corresponding second score of 20.

In the examples provided herein, each second score is determined based on corresponding tooth's crown length, gingival attachment length, root length, root tip length, recession, and pocket depth. In practice, however, the second score can also depend on additional factors. For example, in some implementations, the second score can also depend on factors such as whether bleeding is observed in association with the tooth, whether suppuration of the tooth is observed, the degree of tooth mobility observed, and/or the degree of furcation exposure observed with respect to the tooth. In some cases, the second score can be first calculated as shown in the examples described herein, and then modified based on observed bleeding, suppuration, mobility, and/or furcation.

For example, in some cases, the second set of data can include a parameter indicating whether or not bleeding was observed in association with the tooth. In some cases, determining whether or not bleeding is associated with a tooth can be based on a particular standard or established criterion. For example, in some implementations, if bleeding is observed upon gentle gingival probing, then it determined that there is bleeding associated with the tooth. If the parameter indicates that bleeding was observed, the second score for the tooth can be reduced by a particular pre-determined value (e.g., one). As an example, a tooth having an overall effective root percentage (oERP) of 70% has a corresponding second score of 40. However, if the second set of data includes a parameter indicating that bleeding was observed in association with the tooth, the second score can be reduced to 39.

As another example, in some cases, the second set of data can include a parameter indicating whether or not suppuration of the tooth was observed. In some cases, determining whether or not suppuration is associated with a tooth can be based on a particular standard or established criterion. For example, in some implementations, if any evidence of pus is observed, then it is determined that there is suppuration associated with the tooth. If the parameter indicates that suppuration was observed, the second score for the tooth can be reduced by a particular pre-determined value (e.g., 1.5). As an example, a tooth having an overall effective root percentage (oERP) of 70% has a corresponding second score of 40. However, if the second set of data includes a parameter indicating that suppuration was observed in association with the tooth, the second score can be reduced to 38.5.

As yet another example, in some cases, the second set of data can include a parameter indicating whether or not mobility of the tooth was observed. In some cases, determining whether or not a tooth is mobile can be based on a particular standard or established criterion. For example, in some implementations, this can be a clinical standard (e.g., a standard based on the clinical observations of the dentist). If the parameter indicates that mobility of the tooth was observed, the second score for the tooth can be reduced by a particular pre-determined value (e.g., one). As an example, a tooth having an effective overall root percentage (oERP) of 70% has a corresponding second score of 40. However, if the second set of data includes a parameter indicating that mobility of the tooth was observed in association with the tooth, the second score can be reduced to 39.

In some cases, the parameter indicating whether or not mobility of the tooth was observed can be binary (e.g., indicating either that mobility was observed, or that mobility was not observed). In some cases, this parameter can instead indicate varying degrees of mobility (e.g., a relatively small degree of mobility, a relatively moderate degree of mobility, a relatively large degree of mobility, and so forth). In these implementations, each different degree of mobility can reduce the second score of the tooth by a respective number (e.g., a reduction of one, two, or three for a small, moderate, or large degree of mobility, respectively). In some cases, degrees of mobility can be defined according to a clinical standard (e.g., a standard based on the clinical observations of the dentist). As an example, a tooth having an effective overall root percentage (oERP) of 70% has a corresponding second score of 40. However, if the second set of data includes a parameter indicating that a moderate degree of mobility of the tooth was observed in association with the tooth, the second score can be reduced to 38.

As yet another example, in some cases, the second set of data can include a parameter indicating whether or not the furcation of the tooth was observed. In some cases, determining the degree of furcation exposure can be based on a particular standard or established criterion. For example, in some implementations, this can be a clinical standard (e.g., a standard based on the clinical observations of the dentist). If the parameter indicates that the furcation of the tooth was observed, the second score for the tooth can be reduced by a particular pre-determined value (e.g., twenty). As an example, a tooth having an effective overall root percentage (oERP) of 70% has a corresponding second score of 40. However, if the second set of data includes a parameter indicating that the furcation of the tooth was observed in association with the tooth, the second score can be reduced to 20.

In some cases, the parameter indicating whether or not furcation exposure of the tooth was observed can be binary (e.g., indicating either that furcation exposure was observed, or that furcation exposure was not observed). In some cases, this parameter may indicate varying degrees of furcation exposure (e.g., a relatively small degree of exposure, a relatively moderate degree of exposure, a relatively large degree of exposure, and so forth). In these implementations, each different degree of exposure can reduce the second score of the tooth by a respective number (e.g., a reduction of zero, twenty, or twenty for a small, moderate, or large degree of furcation exposure, respectively). In some cases, degrees of furcation exposure can be defined according to a clinical standard (e.g., a standard based on the clinical observations of the dentist). As an example, a tooth having an effective overall root percentage (oERP) of 70% has a corresponding second score of 40. However, if the second set of data includes a parameter indicating that a moderate degree of furcation exposure was observed in association with the tooth, the second score can be reduced to 20.

In some cases, the second score can be further modified based on a determination of a root to crown ratio of the tooth. For example, the root to crown ratio (RCR) of the tooth can be calculated using the relationship:

$$RCR = \frac{ERL}{ECL} \text{ (\%)}.$$

Although we refer to the relationship ERL/ECL as the root to crown ratio (RCR), this relationship is often alternatively referred to as the crown to root ratio (CRR), particularly in the field of dentistry. For the purposes of this disclosure, we will refer to this relationship as the root to crown ratio (RCR), with the understanding that it may, in some situations, be alternatively referred to as the crown to root ratio (CRR) in practice.

Based on the root to crown ratio (RCR), a modifier score can be calculated and subtracted from the second score. For instance, if RCR is greater than or equal to 67%, the modifier score can be 0. If the RCR is greater or equal to 52% and less than 67%, the modifier score can be 1. If the RCR is less than 52%, the modifier score can be 2. As an example, a tooth having an overall effective root percentage (oERP) of 70% has a corresponding second score of 40. However, if the root to crown ratio (RCR) of the tooth is 55%, the modifier score can be 1; thus, the second score can be reduced to 39.

In some cases, the modifier score can be determined based on a combination of observed bleeding, observed suppuration, observed mobility, observed furcation, and/or the tooth's root to crown ratio (RCR). As an example, a tooth having an overall effective root percentage (oERP) of 70% has a corresponding second score of 40. However, if the root to crown ratio (RCR) of the tooth is 55%, the modifier score can be 1; thus, the second score can be reduced to 39. If, in addition, a relatively small degree of mobility of that tooth was observed, the modifier score can be 2; thus, the second score can be reduced to 38. If, in addition, bleeding was observed in association with that tooth, the modifier score can be 3; thus, the second score can be reduced to 37. Thus, the presence or absence of different particular conditions can be collectively considered in determining the modifier score.

In some implementations, if the root to crown ratio (RCR) is less than a particular threshold, the modifier score can have a specific value, regardless of the presence or absence of one or more other conditions (e.g., bleeding, suppuration, and mobility). For instance, in some cases, if the root to crown ratio (RCR) is less than 40%, the modifier score can be 10, regardless of the presence or absence of bleeding, suppuration, and mobility. As an example, a tooth having an overall effective root percentage (oERP) of 70% has a corresponding second score of 40. However, if the root to crown ratio (RCR) of the tooth is 35%, the modifier score is 10; thus, the second score can be reduced to 30, regardless of the presence or absence of bleeding, suppuration, and mobility.

In some cases, if the root to crown ratio (RCR) is less than a particular threshold, the modifier score can depend on the presence or absence of some, but not all, of the aforementioned conditions. For instance, in some cases, if the root to crown ratio (RCR) is less than a particular threshold (e.g., less than 40%), the modifier score can be 10, regardless of the presence or absence of bleeding, suppuration, and mobility. However, if a moderate degree of furcation was observed, the modifier score can be increased (e.g., to 30). As an example, a tooth having an overall effective root percentage (oERP) of 70% has a corresponding second score of 40. However, if the root to crown ratio (RCR) of the tooth is 35%, the modifier score is 10; thus, the second score can be reduced to 30, regardless of the presence or absence of bleeding, suppuration, and mobility. If, in addition, moderate furcation was observed, then the modifier score 30; thus, the second score can be reduced to 10.

Although ranges and scores are provided herein, these are merely illustrative examples. In practice, other scores and ranges can be used, depending on the implementation. Similarly, although example combinations of conditions are described herein, these are used merely to illustrate how scores can be calculated. In practice, other combinations of conditions and scores are also possible, depending on the implementation.

After determining a second score for each tooth, the process 100 continues by determining a second aggregate score based on the second scores (step 160). In some implementations, the second aggregate score can be determined by first determining the average of the individual second scores. In determining an average, the second score corresponding to missing teeth can be excluded from the average. Thus, in these cases, missing teeth will not be factored into the average of the second scores. This can be useful, for example, in determining the periodontal health based only on the teeth that are present in the mouth. Although a second aggregate score can be determined based on multiple second scores, in some case, a second aggregate score can be determined based on a single second score (e.g., a first score for a single tooth).

After the average of the second scores is calculated, the average is used to select one of several possible periodontal health categories, where each category indicates a different periodontal health state of the patient. As an example, in some cases, the categories can include a "healthy" category (e.g., indicating relatively high periodontal health), a "Periodontitis Type II—Early" category (e.g., indicating the early onset of periodontitis II), a "Periodontitis Type II—Moderate" category (e.g., indicating moderate periodontitis type II), and a "Periodontitis Type II—Advanced" category (e.g., indicating advanced periodontitis type II). In some cases, each category can be defined according to a range of potential averages. Thus, based on the determined average, a particular category can be selected. As an example, in some cases, a "healthy" category can be defined by averages greater than or equal to 35, a "Periodontitis Type II—Early" category can be defined by averages greater than or equal to 30 and less than 35, a "Periodontitis Type II—Moderate" category can be defined by averages greater than or equal to 20 and less than 30, and a "Periodontitis Type II—Advanced" category can be defined by averages less than 20.

In some implementations, the categories can also include a category for gingivitis. The category for gingivitis can be selected, for example, if the sum of tooth sites where bleeding was observed exceeds one-half of the total sites being examined. In some implementations, the observation of periodontitis and gingivitis can be prioritized when selecting a periodontal health category. For example, when both periodontitis and gingivitis are observed, the periodontitis observation can have a higher priority. Thus, the periodontal health category corresponding to the degree of periodontitis is selected. As another example, when only gingivitis is observed, the periodontal health category corresponding to gingivitis is selected.

Once a category has been selected, the selected category can be used to determine the second aggregate score. In some cases, each category is assigned a particular value (e.g., 1 for "healthy," 2 for "gingivitis" (in the absence of Periodontitis), 3 for "Periodontitis Type II—Early," 4 for "Periodontitis Type II—Moderate," and 5 for "Periodontitis Type II—Advanced"). This value can be used as the second aggregate score. As an example, a patient having an average of second scores of 40 would have a corresponding second aggregate score of 1. As another example, a patient having an average of second scores of 25 would have a corresponding second aggregate score of 4.

Although example categories (and corresponding ranges of averages and second aggregate scores) are described herein, these are merely illustrative examples. In practice, other categories (e.g., a greater number or a fewer number of categories) can be used, depending on the implementation. Likewise, each range of averages and each second aggregate score can also differ, depending on the application. Further, although various categories labels are described herein, these are merely example labels that can be used to describe each category. In practice, other labels can be used, depending on the implementation. Further, in some cases, one or more teeth can be excluded, such that data is not collected for these teeth and/or such that the condition of those teeth does not affect the calculation of the second aggregate score.

After determining a second aggregate score, the process 100 continues by determining a dental health score based on the first aggregate score and the second aggregate score (step 170). The dental health score can indicate the overall dental health of the patient. In some cases, the dental health score can be determined by adding the first aggregate score (representing the hard tissue health of the patient) to the second aggregate score (representing the periodontal health of the patient).

In the examples described herein, the first aggregate score is represented in increments of ten (e.g., 10, 20, 30, and 40), while the second aggregate score is represented in increments of one (e.g., 1, 2, 3, 4, and 5). Thus, adding the first aggregate score and the second aggregate score results in a two digit number that expresses the patient's hard tissue health in the tens place, and the patient's periodontal health in the units place. Thus, based on a single number, a user (e.g., a dentist, an administrator, a patient, or any other user), can readily ascertain the patient's hard tissue health and periodontal health.

As an example, FIG. 3 shows a table 300 that includes several categories 310a-d that are used to calculate a first aggregate score on one axis (representing the hard tissue health of the patient), and several categories 320a-e that are used to calculate a second aggregate score on a second axis (representing the periodontal health of the patient). As shown in FIG. 3, the resulting dental health scores 330 expresses the patient's hard tissue health in the tens place, and the patient's periodontal health in the units place.

After determining a dental health score, the process 100 continues by presenting the dental health score to a user (e.g., a dentist, an administrator, a patient, or any other user) for review (step 180). This can be performed, for example, by presenting the dental health score on an electronic display device (e.g., an LCD screen, an LED screen, a CRT screen, or some other suitable electronic display device). In some implementations, the dental health score can be presented on a physical medium (e.g., printed on a piece of paper or plastic film). In some cases, the score can be presented using visual feedback (e.g., using a display device), auditory feedback (e.g., using an audio playback device, such as a speaker), and/or haptic feedback (e.g., using a device that generates vibrations or other forces in order to present information). The dental health score (as well as each of the intermediate parameter values) also can be stored for later retrieval (e.g., using one or more electronic databases). In some cases, this information can also be made available to other computer systems or applications through an application programming interface (API), which defines what types of information can be transmitted, and how the information can be requested.

In some cases, some or all of the measurements used to determine the dental health score can be obtained using one or more dental instruments, such as a dental probe. For example, in some implementations, information used to determine the dental health score can be collected using the an electronic system that automatically or semi-automatically collects data regarding a patient's teeth based on the placement of a probe or other measuring device against a specific portions of a patient's teeth. Data collected by this system can be made available for use in determining the dental health score (e.g., through an API, through manual data entry, or any other technique for transmitting data). As an example, in some cases, the Florida Probe system (manufactured by Florida Probe Corporation, Gainesville, Fla.) can be used to obtain some or all of the measurements used to determine a patient's dental health score, and the measurements can be transmitted to a computer system to determine the patient's dental health score.

In some cases, the dental health score can be used to determine a course of treatment for the patient. For example, in some cases, each dental health score can be associated with one or more corresponding courses of treatment that are appropriate for a patient having that dental health score. Thus, in determining a dental health score of a particular patient, one or more appropriate courses of treatment for the patient can also be determined, and the patient can be treated in accordance with the determined course of treatment.

The dental health score need not be the only information used to determine an appropriate course of treatment. In some cases, a dentist can use the dental health score along other information in order to make such a determination (e.g., a patient's demographic information, information from current and past examinations, previously determined dental health scores, and so forth). In some cases, the dental health score can be used as an objective measure that enables a dentist to make objective, evidence-based decisions, in the context of other available information, as to when a clinical condition merits treatment versus continued observation.

As an example, periodontal disease is a chronic, incurable disease which results from bacterial infection that, at some level, affects the majority of people throughout the world. If the disease process has been initiated, active intervention may arrest its progression. The nature of this intervention may vary based on a dentist's experience and the specific nature of the infection. Since the nature of the disease is chronic, there may be signs of the disease present from examination to examination, even when the disease has been arrested and the patient considered to be stabilized. Furthermore, these signs may vary from examination to examination. As such, the dentist may be viewing a different manifestation of the same level of disease, or a more progressed presentation.

In many cases, after such observations, "clinical experience" (e.g., knowledge based on a dentist's experience in treating patients in the past) is often an important factor in accurately evaluating a disease and determining an appropriate course of treatment. Dentists, however, may vary greatly on how that experience is applied. For example, in some cases, even when multiple dentists may have similar clinical experience, each of the dentists will often have varying opinions as to the locations, severities, and nature of the disease presentation.

An advantage of the dental health score is that, in certain implementations, the score can provide an objective standard for determining when the level of disease has significantly changed based on predetermined criteria.

Combined with other factors (e.g., a patient's age, and archived data from the patient's past examinations), the dental health score can provide information regarding the rate of carious and periodontal destruction. As such, this allows the dentist to objectively determine whether these disease presentations are actively progressing, or in remission, based on whether the rate of health deterioration exceeds an age-based comparison or a comparison from visit to visit. An appropriate treatment can then be selected after considering this information.

Implementations of the process 100 can be performed by one or more computer systems (e.g., a single computer system, or several interconnected computer systems, such as a "cloud" computer system). In some cases, the process 100 can be performed by one or more computer systems based on data inputted by a user. Accordingly, in some cases, a computer system can include a user interface that allows a user to input data into the computer system (e.g., for processing and/or storage), transmit commands to the computer system, and receive feedback from the computer system.

Figure 4B:
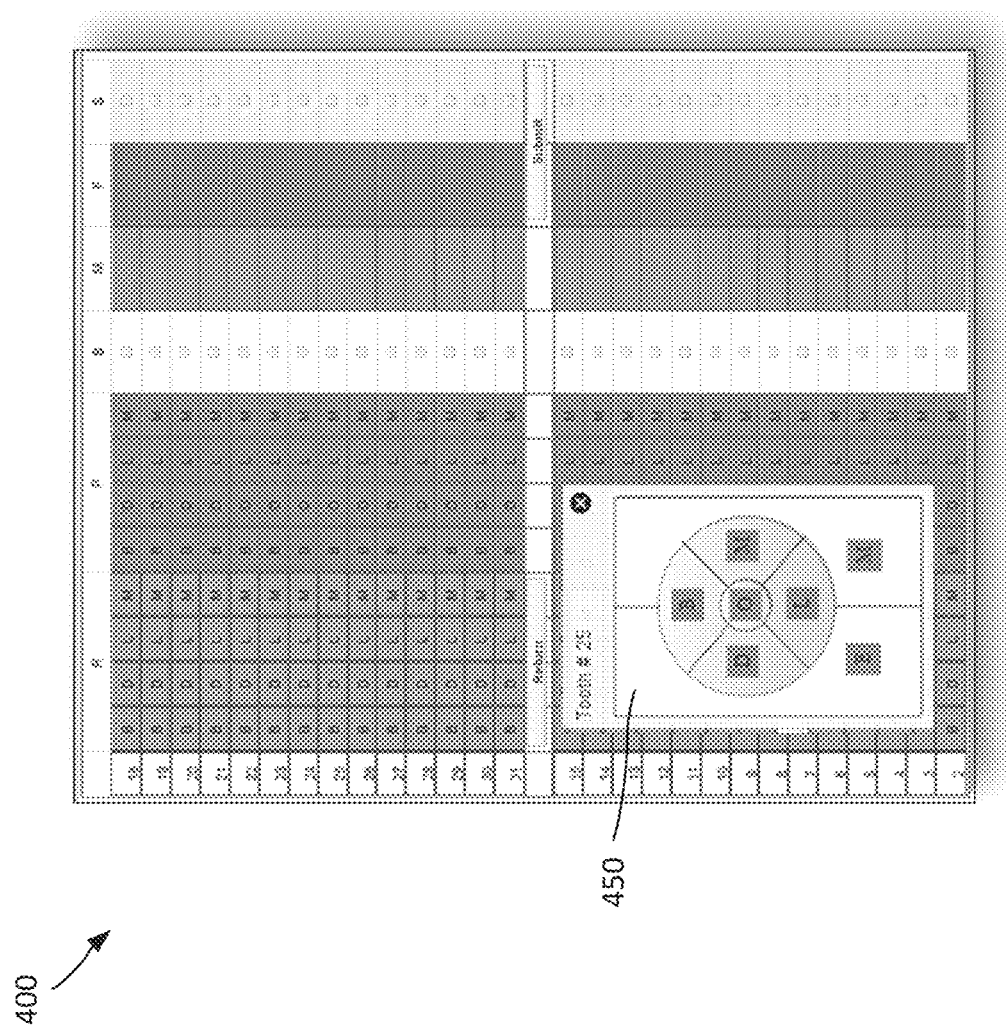

An example user interface 400 for inputting data is shown in FIGS. 4A-B. In this example, the user interface 400 includes a table 410, where each row 420 of the table 410 corresponds to a different tooth of a patient, and where each column 430 of the table 410 corresponds to a different parameter associated with the teeth. Accordingly, each cell 440 corresponds to a particular parameter value associated with a particular tooth. The user can thus enter data into the computer system by entering data into each of the cells 440 (e.g., by selecting a particular cell 440 and entering information using an input device such as a mouse or keyboard). In the user interface 400 shown in FIG. 4A, each of the numbers shown in the leftmost side of rows 420 indicates a particular tooth, and each of the labels shown in the uppermost side of the columns 430 indicates a particular parameter value (e.g., where R, P, B, M, F, and S correspond to recession, pocket depth, bleeding, mobility, furcation involvement, and suppuration, respectively). Further, for some parameter values (e.g., recession and pocket depth), information can be entered to each of several sides of a tooth (e.g., where B, D, L, and M correspond to buccal, distal, lingual, and mesial sides, respectively).

In some cases, the user can enter data using a graphical representation of a tooth. As an example, the user interface 400 shows a graphical representation of a tooth 450, that visually displays various surfaces of a tooth (e.g., where B, D, L, M, and O correspond to buccal, distal, lingual, mesial, and occlusal sides, respectively of the tooth, and E and M represent "excluded" and "missing," respectively). In some cases, the graphical representation 450 is a pop-up element that is revealed when the user selects a particular tooth. The user can thus enter data into the computer system by selecting a particular tooth (e.g., by selecting a particular row 420, and selecting particular surfaces of a tooth using the graphical representation 450). For instance, the user can toggle particular portions of the graphical representation 450 to indicate whether certain surfaces are damaged/missing, or healthy. Although a pop-up graphical representation 450 is shown in FIG. 4B, data can be entered using other interface elements, either instead of or in addition to the pop-up graphical representation 450. For example, in some cases, the interface 400 can include a pull-down menu that appears when the user selects a particular tooth or parameter value. The user can then select an appropriate value from the pull-down to enter data. As another example, in some cases, the interface 400 can include text boxes that allow a user to manually input data (e.g., using a keyboard).

In some cases, the computer system can include a user interface that presents patient information to a user. An example user interface 500 for displaying information is shown in FIGS. 5A-E. The user interface 500 includes a region 510 for displaying information regarding the health status of each tooth, a region 520 for displaying medical images associated with the patient (e.g., X-ray images of the patient's teeth), and a region 530 for displaying other images associated with the patient (e.g., photographs of the patient and/or the patient's teeth). The user interface 500 also includes a navigation region 540 that allows a user to navigate between different windows or views (e.g., to access particular functions of the computer system that are not shown in the user interface 500). The user interface 550 also includes a data entry region that allows the user to input various types of information (e.g., various parameter values associated with the patient) into the computer system.

As described herein, the region 510 displays information regarding the health status of each tooth. In the example shown, the region 510 includes a graphical representation of each tooth. The health of each tooth can be indicated in a variety of ways, for example through a color code or symbol code. For instance, teeth that have a relatively healthy prognosis can be indicated by a green color, teeth with a less healthy prognosis can be indicated by a yellow color, teeth with an even less healthy prognosis can be indicated by a red color, excluded teeth can be indicated by a gray color, and missing teeth can be indicated by a crossed-out symbol. In some cases, each tooth can be represented by multiple color codes or symbol codes, each representing a different aspect of the tooth. For example, the hard tissue health of a tooth can be represented by a first color code, while the periodontal heath of the tooth can be presented by a second color code. This can be presented in the region 510 by presenting two color codes for each tooth (e.g., by stacking one color code above the other).

Figure 5A:
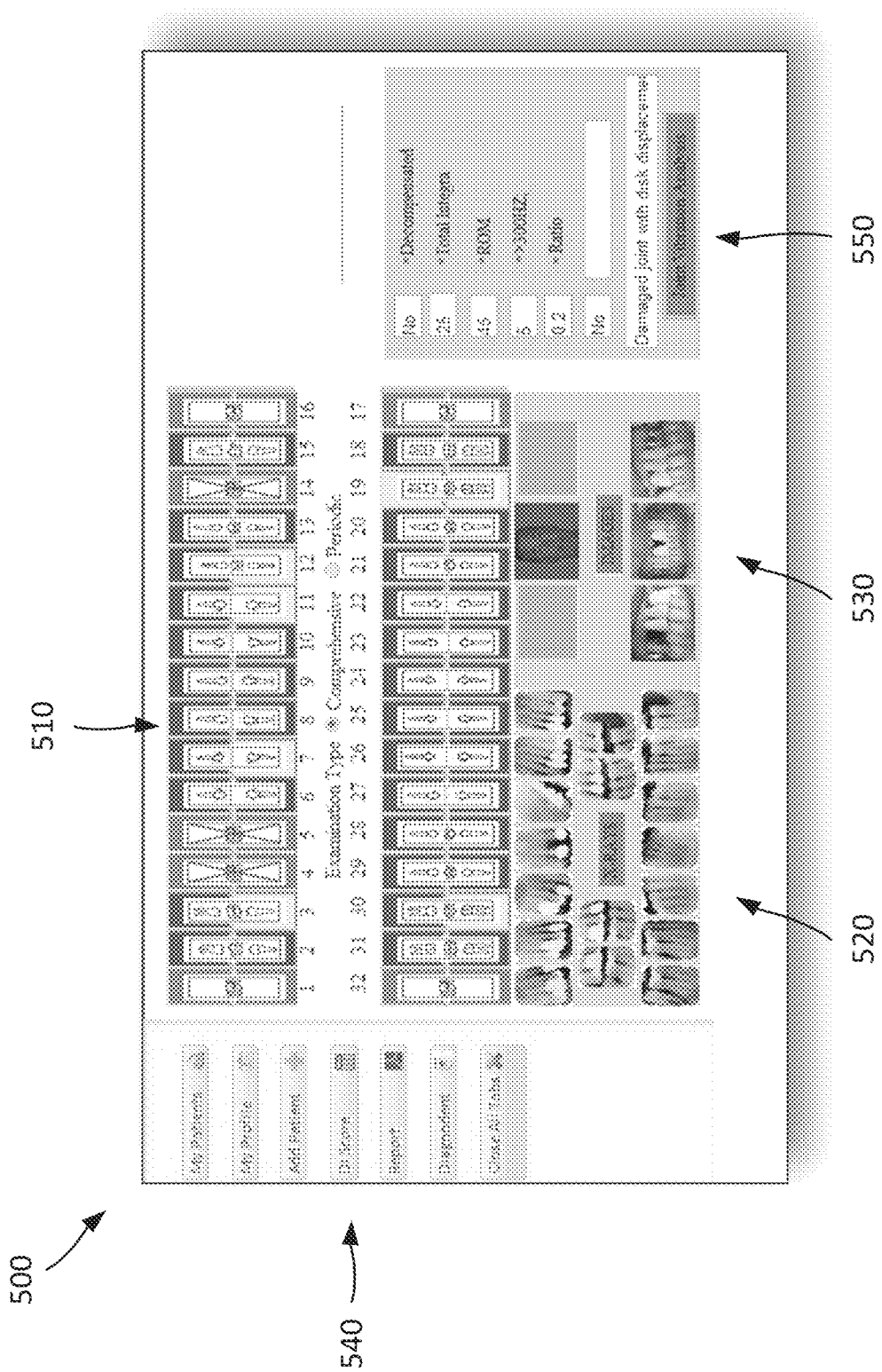
FIGS. 5A, 5B, 5C, 5D, and 5E are screen shots illustrating examples of user interfaces for displaying data.
Figure 5B:
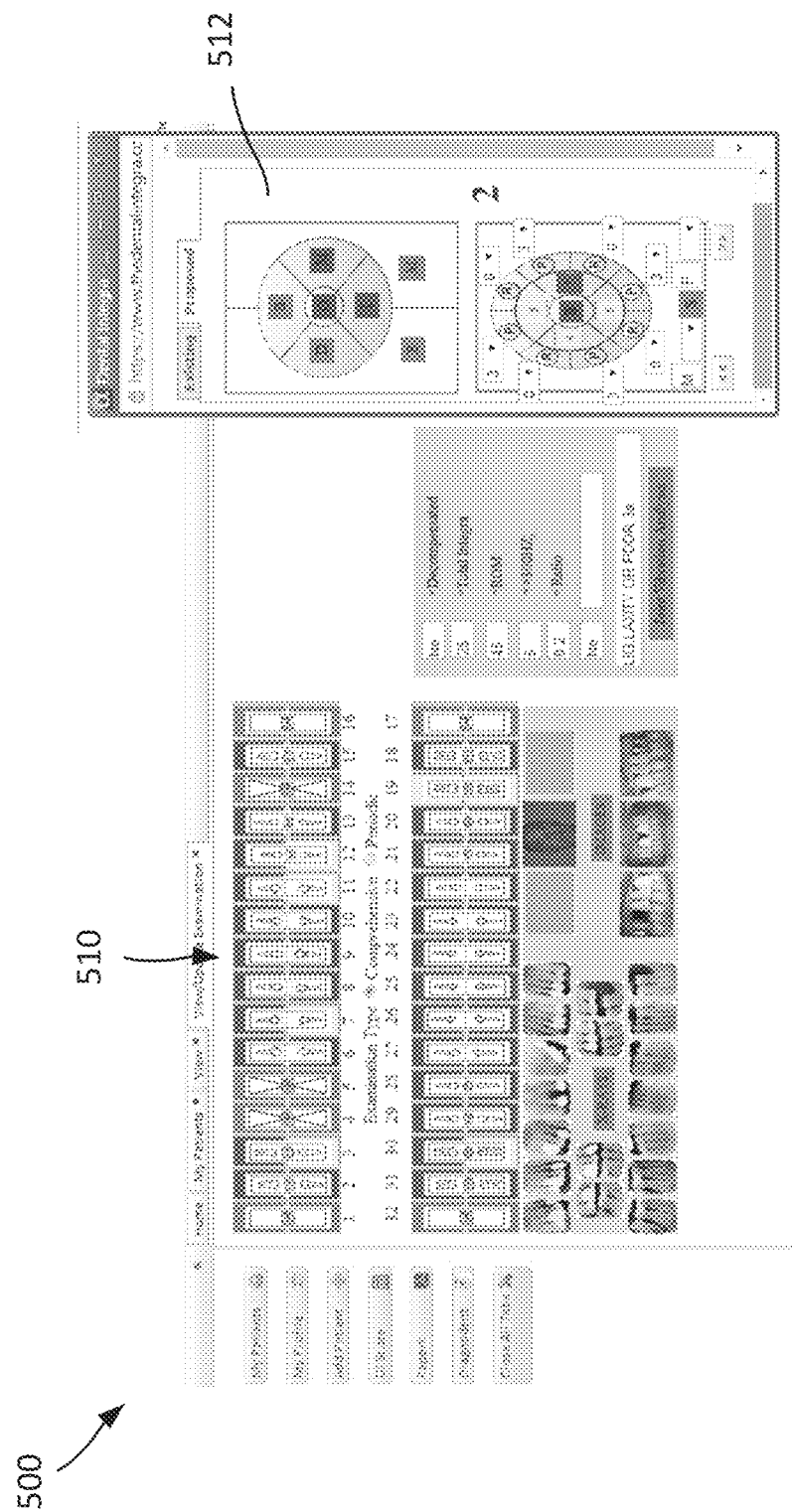
Figure 5C:
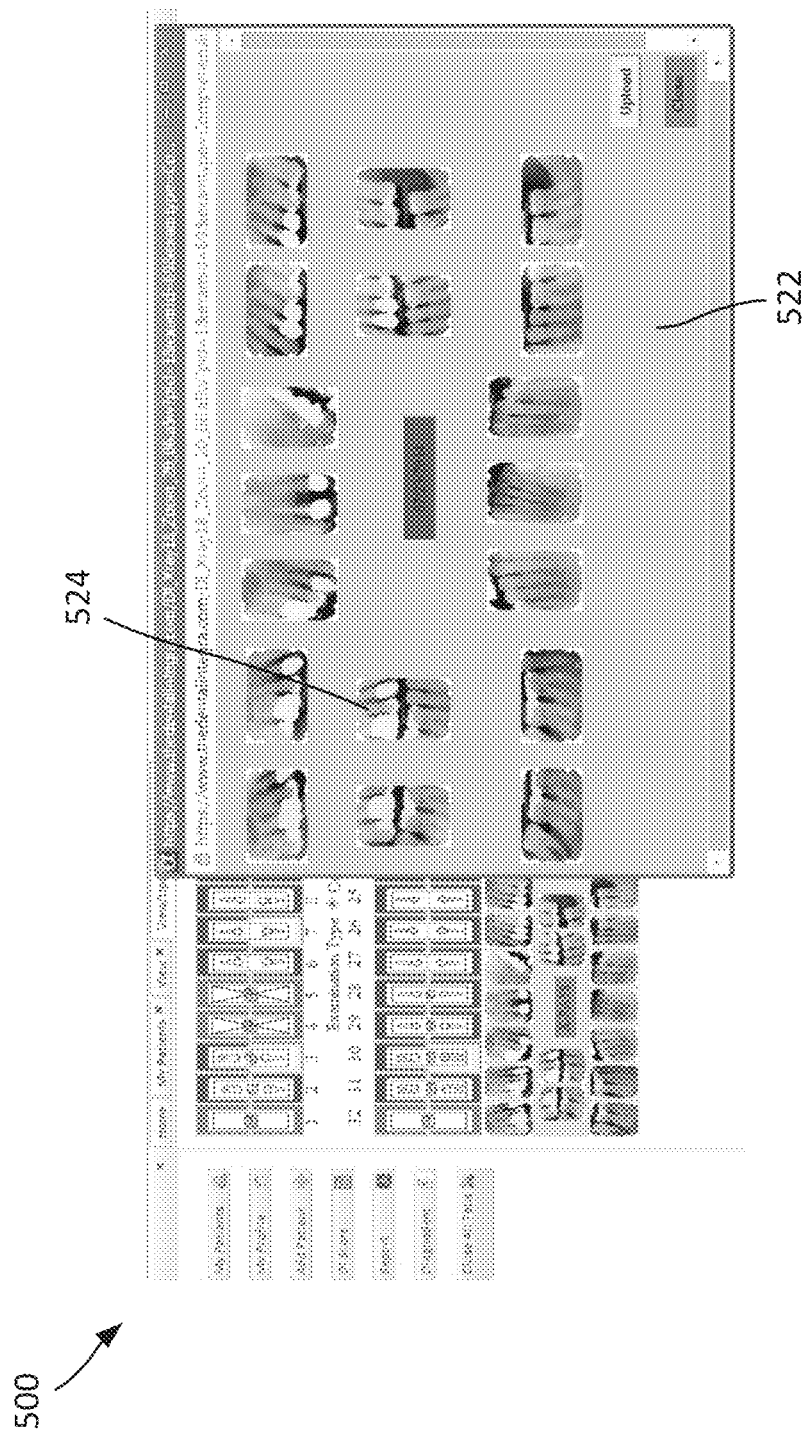

In some cases, the user can also input and/or modify information regarding each tooth using the region 510. For example, as shown in FIG. 5B, the user interface 500 can include a graphical representation 512 of a tooth that visually displays various surfaces of a tooth (e.g., where B, D, L, M, and O correspond to buccal, distal, lingual, mesial, and occlusal sides, respectively of the tooth, and E and M represent excluded" and "missing," respectively). In some cases, the graphical representation 512 is a pop-up element that is revealed when the user selects a particular tooth shown in region 510. The user can thus enter data into the computer system by selecting a particular tooth (e.g., by selecting a particular tooth shown in region 510, and selecting particular surfaces of a tooth using the graphical representation 512). For instance, the user can toggle particular portions of the graphical representation 450 to indicate whether certain surfaces are damaged/missing, or healthy.

In the example shown in FIG. 5B, the graphical representation 512 can also include input areas for accepting additional information other than surface information, for example input areas for accepting information regarding a tooth's recession, pocket depth, bleeding, mobility, furcation involvement, and suppuration. In some cases, the graphical representation 512 can also be used to input the degree to which a particular condition is observed (e.g., the magnitude of recession, the extent of the pocket depth, the degree of bleeding, the degree of mobility, the degree of furcation involvement, and the degree of suppuration). In some cases, these parameters can be represented as a binary value (e.g., indicating "true" or "false," such as the presence or absence of a particular condition), as a number from among a continuous range of numbers (e.g., a value selected from a continuous range), or as a number from among a discrete range of numbers (e.g., a number representing a particular discrete degree, category, or grade amongst multiple different degrees, categories, or grades). For example, in some cases, bleeding and suppuration can be represented by a binary parameter value (e.g., indicating whether or not they were observed), pocketing and recession can be represented by a discrete or continuous parameter value (e.g., indicating a length or depth), while mobility and furcation can be represented by a discrete parameter value (e.g., indicating a particular degree or grade per professional industry standards).

In some cases, some observations can be entered for each of the tooth's sides (e.g., for each of the tooth mesial, distal, buccal, and lingual sides), while some observations can be entered for the tooth as a whole. As an example, in some cases, recession and pocketing are observed for each of a tooth's side, with only the greatest observed value being recorded.

In some cases, the degree to which a particular condition is observed can be recorded as a binary value, even if there may be differences in each occurrence of the condition. As an example, in some cases, furcation involvement can be graded according to particular scale (e.g., 1, 2, and 3), but only furcation involvement having a certain grade (e.g., 2 and 3) are recorded as a positive observation of the condition (e.g., "true"), while other grades (e.g., 1) are recorded as a negative observation of the condition (e.g., "false"). In this manner, certain parameters can be simplified for recordation purposes, even if multiple different categories or grades potentially exist.

Figure 5D:
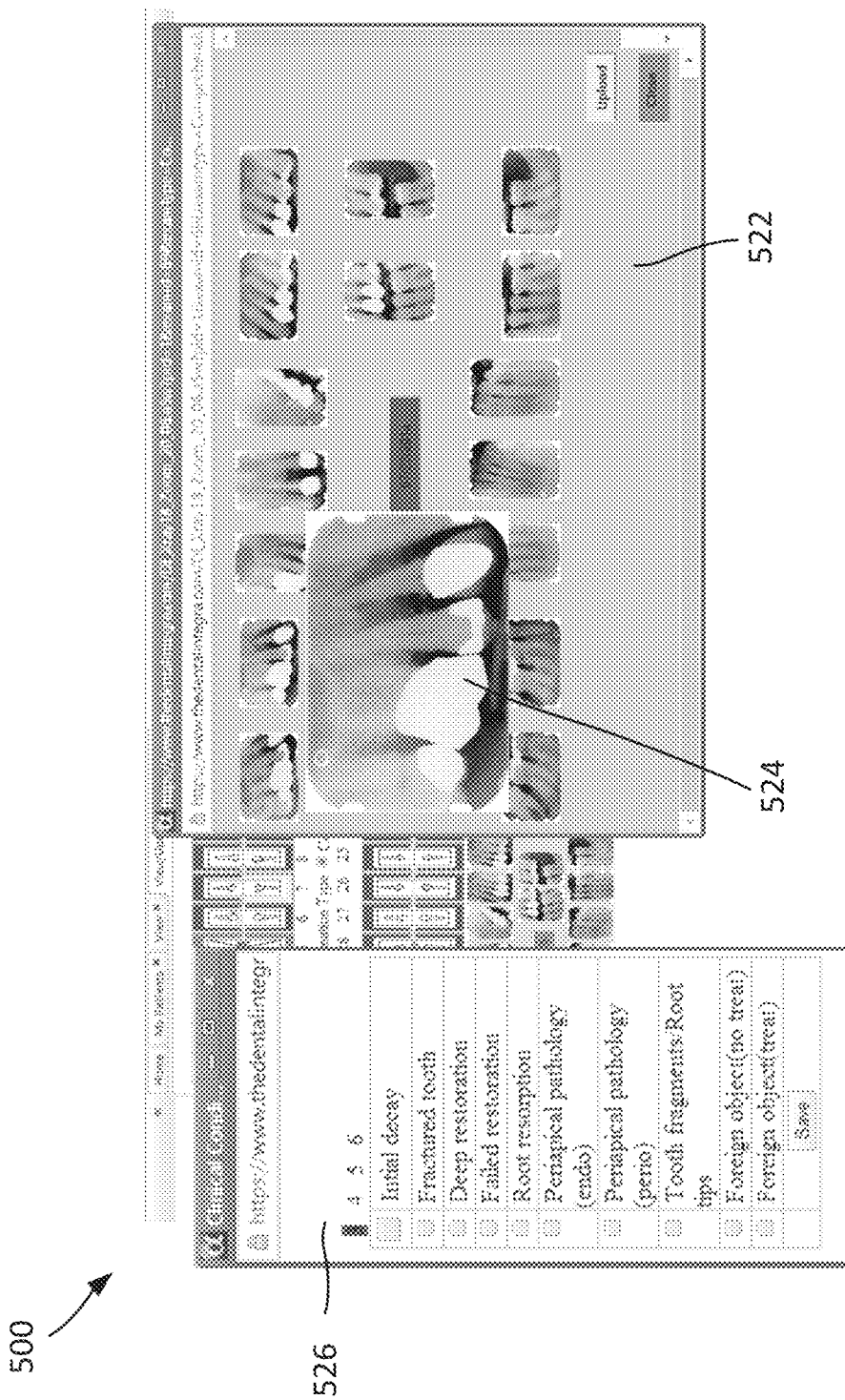

As described herein, the region 520 displays medical images associated with the patient. For example, the region 520 can display various X-ray images of the patient's teeth. In some cases, when the user selects the region 520 (e.g., using an input device such as a mouse or keyboard), the user interface 500 presents one or more medical images in a pop-up window 522. For instance, the pop-up window 522 can display one or more X-ray images 524 within the pop-up window 522. As shown in FIG. 5D, the user can select a particular X-ray image 524 shown in the pop-up window 522 to view the selected X-ray image 524 in greater detail (e.g., as an expanded image). The user can also use a pop-up window 526 to select one or more conditions that he observes in the X-ray images presented in the region 520.

Figure 5E:
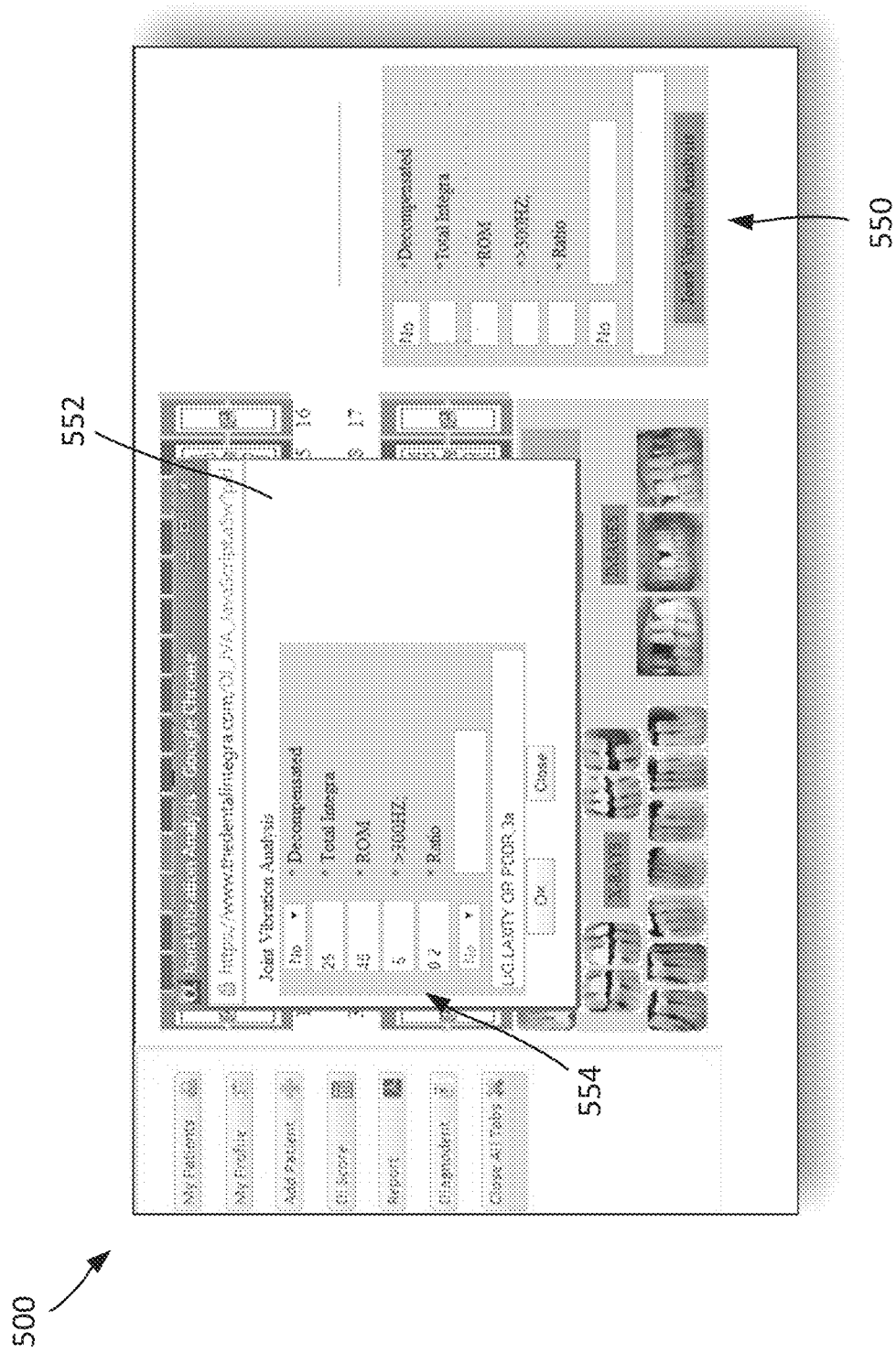

The user interface 500 also includes a data entry region 550 that allows the user to input various types of information into the computer system. For example, the region 550 can include data entry elements that accept user input, such as one or more parameter values that are associated with the patient or information regarding one or more examinations or evaluations that were performed on the patient. As shown in FIG. 5E, in some cases, when the user selects the region 550 (e.g., using an input device such as a mouse or keyboard), the user interface 500 presents a pop-up window 552 that the user can interact with in order to input data. In this example, the pop-up window 552 includes several data entry fields 554. The user can select one or more or the data entry fields 554, and enter data (e.g., using an input device such as a mouse or keyboard).

As described herein, in some cases, the region 550 can accept user input regarding one or more examinations or evaluations that were performed on the patient. This can include information from any examination or evaluation that is relevant to the dental health or general health of a patient. As an example, an examination can be performed using a Diagnodent™ diagnostic device (trademarked by KaVo Dental, Charlotte, N.C.). The Diagnodent™ device includes a non-cutting laser that, when calibrated and shined on the occlusal surface of a tooth, yields information about that tooth's structural integrity. In some cases, if the dentino-enamel junction is generally intact, the device emits a low level noise and indicates a relatively low measurement value (e.g., less than 30, from a scale of 0 to 99). As this junction deteriorates (e.g., as a result of dental caries), this noise becomes higher pitched and the measurement value might increase (e.g., as high as 99). Thus, the Diagnodent™ can provide useful information regarding the health of that tooth. Accordingly, a user can perform an examination using the Diagnodent™ device, and input one or more of the obtained measurement values for future review using the user interface 500.

As another example, a Joint Vibration Analysis (JVA) examination (developed by BioResearch Associates, Inc., Milwaukee, Wis.) can be performed on a patient in order to determine the health of a patient's temporomandibular joints. In a JVA examination, it is assumed that healthy temporomandibular joints, with articular disks and ligaments intact, make relatively little to no "noise" or vibrations during normal function. Normal function, in some cases, is acknowledged to be the ability to open, without discomfort or significant lateral deviation, greater than 40 mm from incisal edge to incisal edge when measured on the slant. By measuring the range of motion and the intensity of a vibration as the patient opens and closes his jaw, the health of the temporomandibular joints can be assessed. Thus, a JVA examination can provide useful information regarding the overall health of the patient's temporomandibular joints. Accordingly, a user can perform a JVA examination, and input one or more of the obtained measurement values for future review using the user interface 500.

Implementations of the user interface 400 and 500 allow a user to enter data regarding each tooth quickly and efficiency. As an example, using the Universal system of dental tooth nomenclature, a user may observe that tooth #18 exhibits one millimeter of recession on the buccal side of the tooth. This can be described as "18-R-B-1," where "18" indicates the tooth number, "R" indicates an observation of recession, "B" indicates that recession was observed on the buccal side of the tooth, and "1" indicates the amount of recession observed. Correspondingly, the user (or the user's assistant) can enter this observation using the user interfaces 400 and/or 500, and entering the appropriate commands (e.g., by selecting portions of the user interface or typing keystrokes corresponding to 18, R, B, and 1).

As another example, a user may observe that tooth #19 exhibits bleeding. This can be described as "19-B" where "19" indicates the tooth number, and "B" indicates an observation of bleeding. Correspondingly, the user (or the user's assistant) can enter this observation using the user interfaces 400 and/or 500, and entering the appropriate commands (e.g., by selecting portions of the user interface or typing keystrokes corresponding to 19 and B).

As yet another example, a user may observe that the tooth #20 exhibits a five millimeter periodontal pocket on the mesial side. This can be described as "20-P-M-5," where "20" indicates the tooth number, "P" indicates an observation of periodontal pocket, "M" indicates that pocket was observed on the mesial side of the tooth, and "5" indicates the depth of the pocket that was observed. Correspondingly, the user (or the user's assistant) can enter this observation using the user interfaces 400 and/or 500, and entering the appropriate commands (e.g., by selecting portions of the user interface or typing keystrokes corresponding to 20, P, M, and 5).

As yet another example, a user may observe that tooth #21 exhibits mobility (corresponding to a degree of mobility 2 out of 3), and exhibits furcation involvement (corresponding to a degree of furcation involvement 3 out of 3). This can be described as "21-M-2," and "21-F-3" respectively. Correspondingly, the user (or the user's assistant) can enter this observation using the user interfaces 400 and/or 500, and entering the appropriate commands (e.g., by selecting portions of the user interface or typing keystrokes corresponding to 21, M, and 2, or 21, F, and 3, respectively).

In some cases, the user interface can present user-selectable elements in the form of a grid or coordinate system, and the user can select one or more of these elements to record his observations. In some cases, the user can use spoken commands to record his observations (e.g., by speaking into a microphone connected to a computer system), and the computer system can transcribe the user's spoken commands and update the user interfaces 400 and/or 500 accordingly.

Although example user interfaces are described herein, these are merely examples to illustrate how a user can interact with a computer system to input and review data. In practice, user interfaces can differ in appearance and functionality, depending on the implementation. For example, in some cases, a user interface can include additional portions, either in addition to or instead of those shown, in order to provide different data entry and/or presentation capabilities. For instance, a user interface can include additional portions that allow a user to enter, modify, and/or delete any information associate with a patient, such that a user can use the computer system to maintain a complete dental and/or medical chart for each patient. This can include, for example, a record of procedures performed on the patient (including who performed them), written and graphical data of existing conditions and anticipated treatments, relevant imaging (e.g., x-rays and photographs), testing data (e.g., the results of various examinations and assays), prescribed medications, and clinical summaries (e.g., summaries including diagnostic impressions).

Figure 6:
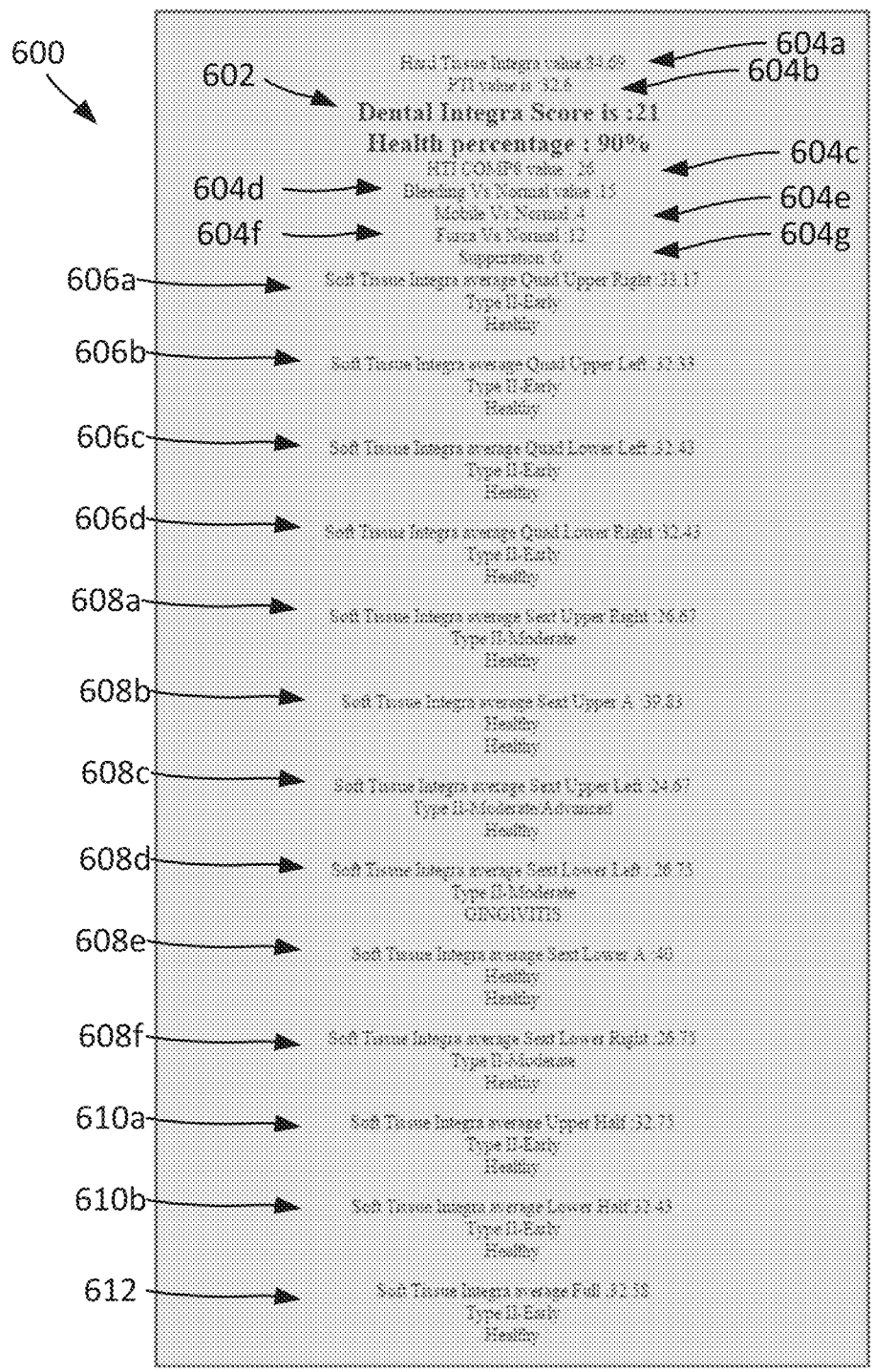
FIG. 6 is a screen shot illustrating an example of a user interface for presenting information regarding the dental health of a patient.

As described herein, a computer system can perform implementations of the process 100 in order to determine a dental health score for a patient. Although the dental health score can be expressed as a single number, in some cases, it may be beneficial to provide the user with additional information regarding how a particular score was determined. This can be useful, for example, to educate a relatively inexperienced user regarding the different factors and criteria that are used to calculate the dental health score, and/or to display additional patient information to a user for a more detailed review. This can also be useful, for example, to present information regarding each of the different regions of a patient's mouth, such that the user can more readily identify problematic regions. As an example, FIG. 6 shows a user interface 600 that represents the determined dental health score of a patient. The user interface 600 presents the determined dental health score 602, as well a summary of the various factors and criteria that were used to calculate the score (e.g., factors 604*a-g*). The user interface 600 also presents a health summary for each of several different regions of the patient's mouth (e.g., each quadrant and sextant of the patient's mouth), such that the user can readily determine the conditions of particular areas of the patient's mouth. For example, the user interface 600 can include a health summaries 606*a-d* for each quadrant of the patient's mouth, health summaries 608*a-f* for each sextant of the patient's mouth, health summaries 610*a-b* for each half of the patient's mouth, and health summary 612 for the entirety of the patient's mouth.

In some cases, the determined dental health score can be used to generate a narrative that describes the dental health of a patient. In some cases, a generated narrative can include a textual and/or visual description of the patient's overall dental health, as well as textual and/or visual descriptions of the patient's specific dental problems or conditions. As an example, the narrative can include a portion that describes the determined dental health score and the criteria that influenced the calculation of the score. The narrative can include one or more portions that describe the user's specific dental problems (e.g., specific teeth or portions of the patient's mouth that are associated with relatively low dental health).

In some cases, the narrative can be generated automatically or semi-automatically. For example, one or more pre-determined passages can be pre-written (e.g., by a dentist or administrator), such that each potential condition (or combination of conditions) of a patient has a corresponding pre-written passages. Based on the determined dental health score, one or more pre-written passages can be automatically selected for inclusion in a narrative for the patient. As an example, a passage can be pre-written for patients having "best" hard tissue health, another passage can be pre-written for patients having "good" hard tissue health, and so forth. Based on the hard tissue health for a given patient, an appropriate pre-written passage can be selected for inclusion in a narrative for that patient. Likewise, a passage can be pre-written for patients that have high periodontal health, another passage can be pre-written for patients suffering for gingivitis, and other passages can be pre-written for patients suffering varying degrees of periodontitis, and so forth. Based on the periodontal health for a given patient, an appropriate pre-written passage can be selected for inclusion in a narrative for that patient. Similarly, pre-written passages can be drafted based on other conditions and criteria (e.g., missing teeth, damage teeth, and so forth), or combinations of one or more conditions and criteria.

In some cases, in addition to describing the health condition of the patient, the passages can also describe recommended courses of action to resolve or otherwise reduce the impact of one or more problems. For example, in some cases, a passage can include information to a patient regarding how he might address certain deficiencies in his dental health. As another example, in some cases, a passage can include information to a dentist regarding how the dentist might address certain problems or issues with a particular patient's dental health. Based on the determined dental health score, one or more appropriate passages can be selected for inclusion in a narrative for that patient.

In some cases, narratives can also be generated based on previously known information regarding a patient. For example, in some cases, a patient's medical history, medication history, examination history, and/or family medical history may be known. Based on these factors, one or more appropriate pre-written passages can be selected for inclusion in a narrative for that patient.

In some cases, portions of the narrative can be completed based on the determined dental health score and other known information regarding the patient, even if a full and complete pre-determined passage is not available. For example, based on a determined dental health score, pre-written passages might be selected based on the hard tissue health category and periodontal health category corresponding with the that score. These pre-written passages might be incomplete, and include blanks, spaces, or placeholders for various additional pieces of information. For example, the passages can include blanks, spaces, or placeholders for the exact dental health score of the patient, the specific tooth locations of the patient (e.g., tooth numbers identifying particular teeth of interest), identifying information regarding the patient (e.g., the patient's name, age, gender, address, telephone number, etc.), or the patient's medical history (e.g., medication history, previously diagnosed illnesses or conditions, etc.) As the narrative is being generated, each of these blanks, spaces, or placeholders can be filled in with the appropriate information. For example, the appropriate information can be automatically or semi-automatically filled in based on the data obtained before, during, or after determination of the patient's dental health score).

In some cases, each pre-written passage can be written in a single language (e.g., English). In other cases, each pre-written passage can have multiple versions, each written in a different language (e.g., English, Spanish, French, German, Mandarin, Hindi, Arabic, and so forth), and an appropriate version can be selected based on the language preferences of the patient, dentist, or other user. In some cases, multiple narratives can be generated such that the dental health of the patient is described in several different languages.

An example narrative 700 is shown in FIGS. 7A-C. The narrative 700 includes several passages 710, each describing a particular topic that is relevant to a particular patient. One or more of the passages 710 can be pre-written, then automatically selected based on the determined dental score and/or other known information regarding the patient, in order to generate a narrative regarding that patient. This narrative 700 can be presented to a dentist, an administrator, the patient, and/or any other person interested in learning more about a particular patient's dental health.

For example, the narrative 700 shown in FIGS. 7A-C includes a passage 710a that provides an introduction to the patient. The passage 710a can include, for example, information regarding the patient's last medical examination (e.g., the date, location, and/or physician that conducted the examination). The passage 710a can also include information regarding the patient's medical provider. The passage 710a can also include a summary of the patient's overall medical condition. In some cases, part of the passage 710a can be pre-written, and part of the passage 710a can be automatically filled in based on known information about the patient. For example, in some cases, the passage 710a can be pre-written, but can include blanks for the date of the patient's last medical examination, medical provider, and medical condition. These blanks can be automatically or semi-automatically filled in based on known information about the patient.

In some cases, the narrative 700 can also include a passage 710b that provides a summary of medical issues that are associated to the patient. The passage 710b can include, for example, information identifying and explaining one or more medical conditions experienced by that patient (e.g., heart disease, diabetes, back problems, or any other medical condition). Again, in some cases, part of the passage 710b can be pre-written, and part of the passage 710b can be automatically filled in based on known information about the patient. For example, in some cases, portions of the passage 710b can be selected from a group of pre-written descriptions for a variety of different medical conditions. These pre-written descriptions can be selected automatically or semi-automatically based on known information about the patient. For example, in some cases, these pre-written descriptions can be filled in based on information provided by the patient on a medical intake form, or based on information obtained from the patient's medical record In some cases, the narrative 700 can also include a passage 710c that provides a summary of medication being taken by the patient. The passage 710c can include, for example, information identifying and explaining one or more medications that the patient is taking, has taken, or will be taking (e.g., clopidogrel, coreg, or any other medical condition). Again, in some cases, part of the passage 710c can be pre-written, and part of the passage 710c can be automatically filled in based on known information about the patient. For example, in some cases, portions of the passage 710c can be selected from a group of pre-written descriptions for a variety of different medications. These pre-written descriptions can be selected automatically or semi-automatically based on known information about the patient. For example, in some cases, these pre-written descriptions can be filled in based on information provided by the patient on a medical intake form, or based on information obtained from the patient's medical record.

In some cases, the narrative 700 can also include a passage 710d that provides a summary of the patient's self-reported dental concerns. The passage 710d can include, for example, information identifying and explaining specific dental conditions that the patient has identified as being problematic to his dental health or comfort (e.g., tender or bleeding gums, tooth sensitivity, or any other condition). Again, in some cases, part of the passage 710d can be pre-written, and part of the passage 710d can be automatically filled in based on known information about the patient. For example, in some cases, portions of the passage 710d can be selected from a group of pre-written descriptions for a variety of dental concerns. These pre-written descriptions can be selected automatically or semi-automatically based on known information about the patient. For example, in some cases, these pre-written descriptions can be filled in based on information provided by the patient on a medical intake form, or based on information obtained from the patient's medical record.

In some cases, the narrative 700 can also include a passage 710e that provides a summary of a radiographic examination performed on the patient. The passage 710e can include, for example, information identifying and explaining specific dental conditions that were observed during the radiographic examination (e.g., evidence of new decay, secondary decay, foreign objects, tooth restoration, ligament integrity, or any other condition), as well as an identification of the region where it was observed (e.g., a specific tooth location or a general location of the mouth). Again, in some cases, part of the passage 710e can be pre-written, and part of the passage 710e can be automatically filled in based on known information about the patient. For example, in some cases, portions of the passage 710e can be selected from a group of pre-written descriptions for a variety of observations that might be made during a radiographic examination, but can include blanks for the specific tooth locations or mouth regions where these observations might be made. These pre-written descriptions can be selected automatically or semi-automatically based on known information about the patient, and the blanks can be automatically or semi-automatically filled in based on known information about the patient. For example, in some cases, these pre-written descriptions can be filled in based on information obtained from a radiographic examination report or the patient's medical record.

In some cases, the narrative 700 can also include a passage 710f that provides a summary of one or more other examinations performed on the patient. The passage 710f can include, for example, information identifying and explaining the results of a temporomandibular joint examination performed on the patient. Again, in some cases, part of the passage 710f can be pre-written, and part of the passage 710f can be automatically filled in based on known information about the patient. For example, in some cases, portions of the passage 710f can be selected from a group of pre-written descriptions for a variety of possible results from the examination. These pre-written descriptions can be selected automatically or semi-automatically based on known information about the patient. For example, in some cases, these pre-written descriptions can be filled in based on information obtained from an examination report or the patient's medical record. Although a temporomandibular joint examination is described herein, this is only an illustrative example. Information regarding other types of examinations can also be included, either instead of or in addition to that described herein.

In some cases, the narrative 700 can also include a passage 710g that provides a summary of the dental health score of the patient. The passage 710g can include, for example, information identifying and explaining the dental health score of the patient. Again, in some cases, part of the passage 710g can be pre-written, and part of the passage 710g can be automatically filled in based on known information about the patient. For example, in some cases, portions of the passage 710g can be selected from a group of pre-written descriptions for a variety of different possible dental health scores, but can include blanks for the specific values or factors that might have gone into determining that score (e.g., the number of tooth surfaces that were damaged, the dimensions of one or more teeth, the observation of various dental conditions, or any of the other factors described herein). These pre-written descriptions can be selected automatically or semi-automatically based on known information about the patient, and the blanks can be automatically or semi-automatically filled in based on known information about the patient. For example, in some cases, these pre-written descriptions can be filled in based on information obtained information obtained before or during the determination of a patient's dental health score (e.g., as described with respect to FIG. 1) or the patient's medical record.

As disclosed herein, example techniques are provided that can be performed with respect to one or more teeth of a patient. However, it is understood that the term "tooth" can also refer to tooth "locations" in the patient's mouth, regardless of whether a tooth is physically present at that location. For instance, one or more of these techniques can be performed with respect to locations of the patient's mouth corresponding to the typical location of teeth in a normal, healthy human. If any teeth are missing, one or more of the described techniques described herein can still be performed with respect to that location as appropriate (e.g., determining that the tooth is missing, determining the state or condition of that location, determining one or more scores for that location, and so forth). This can be beneficial in some cases, as it allows for an objective analysis of a patient's dental health, even if he is missing one or more teeth from one or more locations of his mouth.

Some implementations of subject matter and operations described in this specification can be implemented in digital electronic circuitry, or in computer software, firmware, or hardware, including the structures disclosed in this specification and their structural equivalents, or in combinations of one or more of them. For example, the process 100 can be implemented using digital electronic circuitry, or in computer software, firmware, or hardware, or in combinations of one or more of them. As another example, the user interfaces 400, 500, and 600 can be implemented using digital electronic circuitry, or in computer software, firmware, or hardware, or in combinations of one or more of them. As yet another example, the narratives 700 can be generated using digital electronic circuitry, or in computer software, firmware, or hardware, or in combinations of one or more of them.

Some implementations described in this specification can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some implementations described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal; a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network (e.g., a "cloud" system).

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 8:
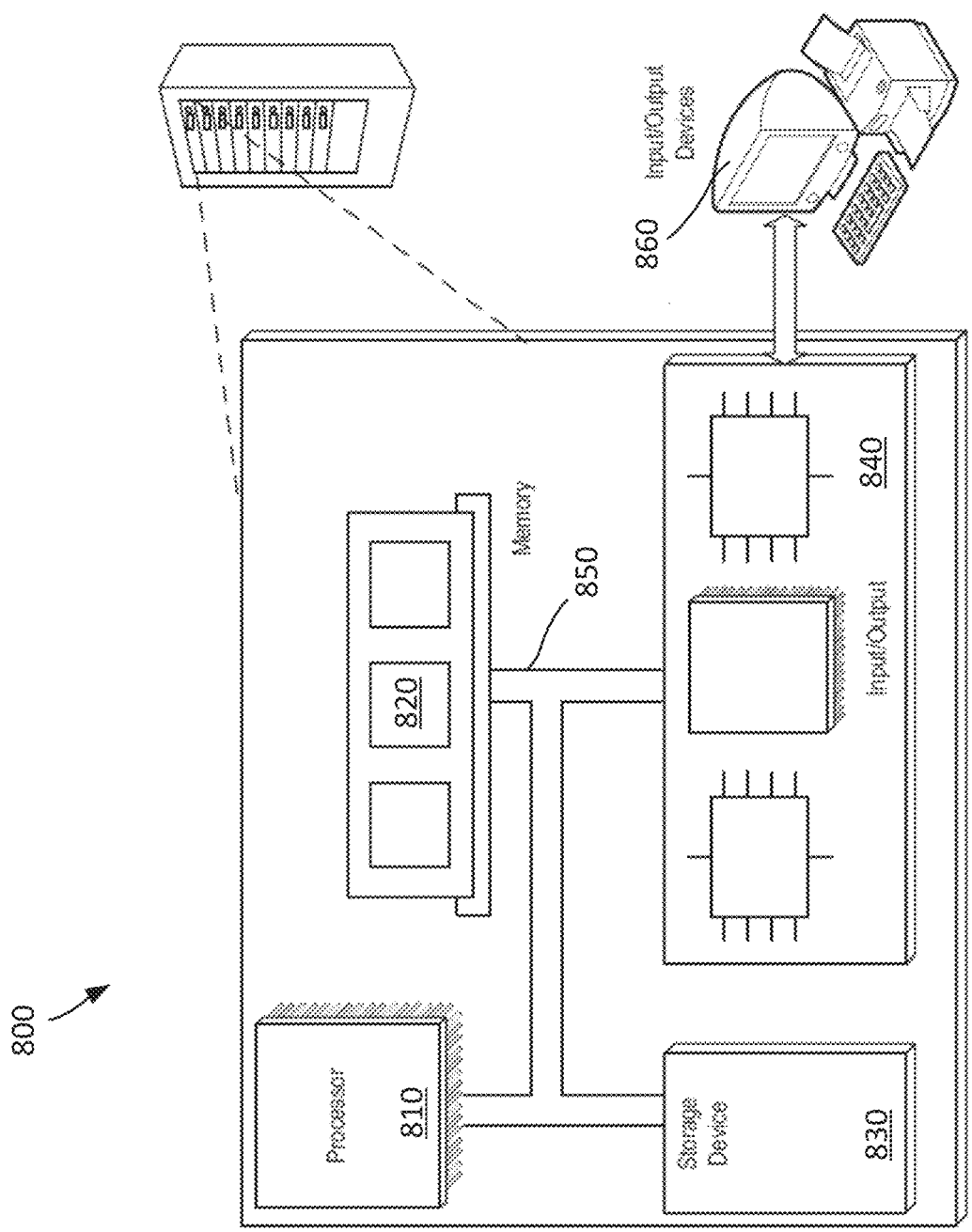
FIG. 8 is a diagram of an example computer system.

FIG. 8 shows an example computer system 800. The computer system 800 can be used, for example, to implement all or part of the process 100. As another example, the user interfaces 400, 500, and 600 can be implemented, at least in part, by the computer system 800. As yet another example, the narratives 700 can be generated, at least in part, by the computer system 800.

The computer system 800 includes a processor 810, a memory 820, a storage device 830 and an input/output device 840. Each of the components 810, 820, 830 and 840 can be interconnected, for example, by a system bus 850. The processor 810 is capable of processing instructions for execution within the system 800. In some implementations, the processor 810 is a single-threaded processor, a multi-threaded processor, or another type of processor. The processor 810 is capable of processing instructions stored in the memory 820 or on the storage device 830. The memory 820 and the storage device 830 can store information within the system 800.

The input/output device 840 provides input/output operations for the system 800. In some implementations, the input/output device 840 can include one or more of a network interface devices, e.g., an Ethernet card, a serial communication device, e.g., an RS-232 port, and/or a wireless interface device, e.g., an 802.11 card, a 3G wireless modem, a 4G wireless modem, etc. In some implementations, the input/output device can include driver devices configured to receive input data and send output data to other input/output devices, e.g., keyboard, printer and display devices 860. In some implementations, mobile computing devices, mobile communication devices, and other devices can be used.

Figure 9:
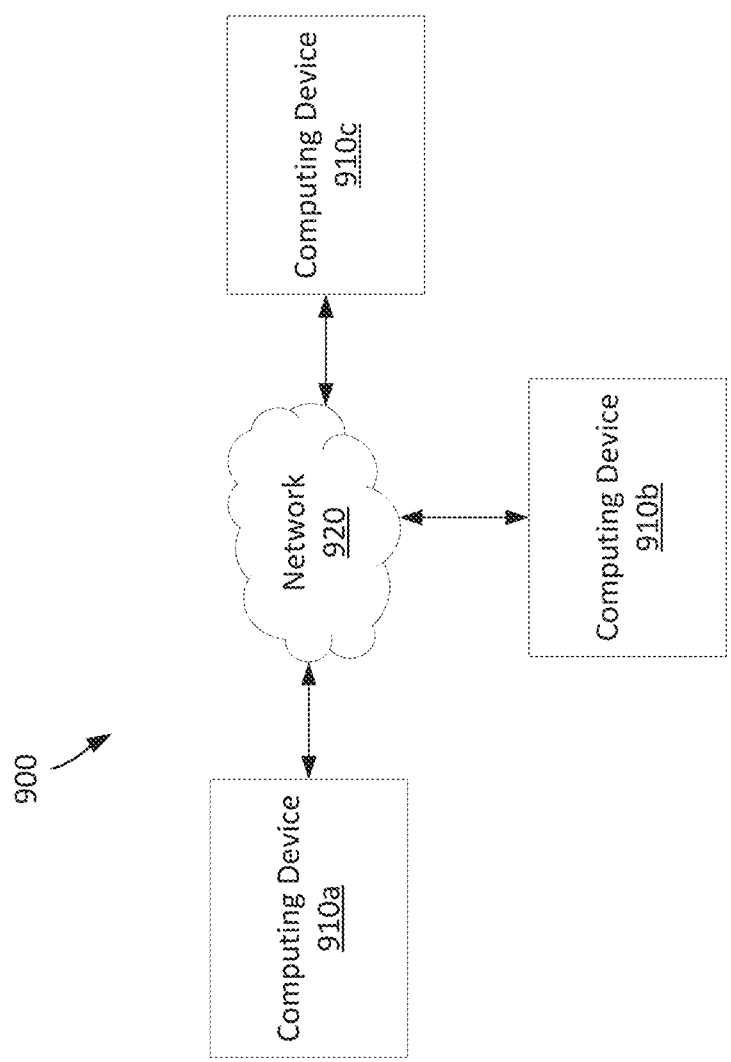
FIG. 9 is a diagram of another example computer system.

As described herein, in some cases, a computer system may include multiple computers that operate in proximity or generally remote from each other. FIG. 9 shows a computer system 900 having an example of such an arrangement. As shown in FIG. 9, the computer system 900 includes three computing devices 910a-c, each communicatively coupled to each other through a communications network 920. The computing devices 910a-c each can be implemented, for example, a similar manner as the computer system 800 shown in FIG. 8. The communication network 920 can be implemented, for example, as described herein.

Each of the computing devices 910a-c can be used to implement one or more of the aspects described herein. For instance, in some cases, a first computing device 910a can perform the process 100, and can receive data from the other computing devices 910b-c in order to perform the process 100. As an example, in some implementations, the computing devices 910b-c can store first and/or second sets of data for one or more patients, and can transmit these data sets of the computing device 910a for analysis using the process 100. As another example, some implementations the computing devices 910b-c can be used to control medical instruments (e.g., a device that controls an instrument such as the Diagnodent™ diagnostic device, the Florida Probe system, or any other medical instrument) and/or process medical data (e.g., a device that performs aspects of a JVA examination), and can transmit data to the computing device 910a for analysis using the process 100. As described herein, in some implementations, data can be transmitted between computing devices 910a-c using an application programming interface (API), which defines what types of information can be retrieved from a particular computing device, and how the information can be retrieved. Although example divisions of tasks are described herein, these are merely examples. In practice, tasks can be performed by any combination of different computing devices.

In some cases, one or more of the computing devices 910a-c can be remote from one or more of the other computing devices 910a-c. For example, in some cases, the computing device 910a-b can be positioned local to each other (e.g., adjacent to each other or within the same room), while the computing device 910c can be positioned remote from the computing devices 910a-b (e.g., within separate rooms, buildings, cities, or countries).

Although three computing devices 910a-c are shown herein, this is merely an illustrative example. In practice, any number of different computing devices can be used to implement the one or more of the aspects described herein. Further, although the example herein shows computing devices 910a-c communicatively coupled through a communications network 920, other forms of communication are also possible. For example, in some cases, some of the computing devices 910a-c can be communicatively coupled through a direct connection between them (e.g., a serial connection, USB connection, and so forth). In some cases, some of the computing devices 910*a-c* can be communicatively coupled through a portable storage medium that receives information from one computing device and transmits the storage information to another computing device (e.g., a portable storage device, such as a portable hard disk, flash memory storage device, optical disc, and so forth).

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of implementations have been described. Nevertheless, it will be understood that various modifications may be made without departing from the spirit and scope of the disclosure. Accordingly, other embodiments are within the scope of the following claims.

What is claimed is:

1. A method of assessing a patient's dental health, the method comprising:
   receiving, at a processor, for each location of a plurality of tooth locations, a corresponding first set of data and a corresponding second set of data,
      wherein the first set of data indicates a physical condition of a tooth at the location, and
      wherein the second set of data indicates a plurality of physical parameters of the tooth at the location;
   determining, by the processor, for each location of the plurality of tooth locations, a first score based on the corresponding first set of data, wherein the first score indicates a hard tissue health state of a tooth at the location;
   determining, by the processor, a first aggregate score based on at least one or more of the first scores, wherein the first aggregate score indicates a hard tissue health state of the patient;
   determining, by the processor, for each location of the plurality of tooth locations, an initial second score based on the corresponding second set of data, wherein the initial second score is determined based on each physical parameter of the plurality of physical parameters of a tooth at the location;
   determining, by the processor, for each location of the plurality of tooth locations, a modified second score, wherein the modified second score indicates a periodontal health state of the tooth at the location, and wherein determining each modified second score comprises:
      receiving, at the processor, an indication that the tooth location is associated with a particular physical characteristic, and
      responsive to receiving the indication, modifying the initial second score for the tooth location based on the indication;
   determining, by the processor, a second aggregate score based at least in part on one or more of the modified second scores, wherein the second aggregate score indicates a periodontal health state of the patient;
   determining, by the processor, a dental health score based on the first aggregate score and the second aggregate score, wherein the dental health score indicates an overall dental health of the patient; and
   outputting the dental health score to a display device.

2. The method of claim 1, wherein each first set of data comprises a parameter specifying a number of surfaces of the tooth at the corresponding location that are damaged or missing; and
   wherein determining each first score is based on the number of surfaces of the tooth at the corresponding location that are damaged or missing.

3. The method of claim 1, wherein determining the first aggregate score comprises:
   summing, by the processor, the first scores;
   selecting, by the processor, a particular hard tissue health category from among a plurality of hard tissue health categories based on the sum of the first scores; and
   determining, by the processor, the first aggregate score based on the selected hard tissue health category.

4. The method of claim 3, wherein each second set of data comprises:
   an average crown length of the tooth at the corresponding location, an average root length of the tooth at the corresponding location, a gingival attachment length of the tooth at the corresponding location, a root tip length of the tooth at the corresponding location, and a combined attachment loss of the tooth at the corresponding location.

5. The method of claim 1,
   wherein the indication that the tooth location is associated with the particular physical characteristic comprises an indication that the tooth at the location exhibits bleeding upon probing; and
   wherein modifying the initial second score for the tooth location comprises reducing the initial second score for the location by a pre-determined value.

6. The method of claim 1,
   wherein the indication that the tooth location is associated with the particular physical characteristic comprises an indication that the tooth at the location exhibits suppuration; and
   wherein modifying the initial second score for the tooth location comprises reducing the initial second score for the location by a pre-determined value.

7. The method of claim 1,
   wherein the indication that the tooth location is associated with the particular physical characteristic comprises an indication of a degree of mobility of the tooth at the location; and
   wherein modifying the initial second score for the tooth location comprises reducing the initial second score for the location by a pre-determined value.

8. The method of claim 1,
   wherein the indication that the tooth location is associated with the particular physical characteristic comprises an indication of a degree of furcation involvement of the tooth at the location; and
   wherein modifying the initial second score for the tooth location comprises reducing the initial second score for the location by a pre-determined value.

9. The method of claim 1,
   wherein the indication that the tooth location is associated with the particular physical characteristic comprises an indication of a root to crown ratio of the tooth at the location; and
   determining a modifier score based on the root to crown ratio of the tooth at the location and wherein modifying the initial second score for the tooth location comprises reducing the initial second score for the location by the modifier score.

10. The method of claim 1, wherein determining the second aggregate score comprises:
   determining, by the processor, an average of the modified second scores for each region of a plurality of regions of a patient's mouth, wherein each average of the modified second scores corresponds to teeth of a different respective region;
   selecting, by the processor, a particular periodontal health category from among a plurality of periodontal health categories based on the averages of the modified second scores; and
   determining, by the processor, the second aggregate score based on the selected periodontal health category.

11. The method of claim 1, wherein determining the dental health score comprises adding, by the processor, the first aggregate score and the second aggregate score.

12. The method of claim 1, further comprising:
   determining, by the processor, a course of treatment for the patient based at least in part on the dental health score.

13. The method of claim 12, further comprising outputting to a display the determined course of treatment as a recommended course of treatment.

14. The method of claim 1, further comprising:
   automatically generating, by the processor, a narrative describing the dental health of the patient based on the dental health score; and
   outputting the narrative to a display device.

15. The method of claim 14, wherein automatically generating the narrative comprises:
   obtaining, by the processor, a plurality of narrative templates, each corresponding to a different dental health condition; and
   automatically selecting, by the processor, at least one of the narrative templates based on the dental health score.

16. A non-transitory computer-readable medium including instructions which, when executed by one or more processors causes:
   receiving, at the processor, for each location of a plurality of tooth locations, a corresponding first set of data and a corresponding second set of data,
      wherein the first set of data indicates a physical condition of a tooth at the location, and
      wherein the second set of data indicates a plurality of physical parameters of the tooth at the location;
   determining, by the processor, for each location of the plurality of tooth locations, a first score based on the corresponding first set of data, wherein the first score indicates a hard tissue health state of a tooth at the location;
   determining, by the processor, a first aggregate score based on at least one or more of the first scores, wherein the first aggregate score indicates a hard tissue health state of the patient;
   determining, by the processor, for each location of the plurality of tooth locations, an initial second score based on the corresponding second set of data, wherein the initial second score is determined based on each physical parameter of the plurality of physical parameters of a tooth at the location;
   determining, by the processor, for each location of the plurality of tooth locations, a modified second score, wherein the modified second score indicates a periodontal health state of the tooth at the location, and wherein determining each modified second score comprises:
      receiving, at the processor, an indication that the tooth location is associated with a particular physical characteristic, and
      responsive to receiving the indication, modifying the initial second score for the tooth location based on the indication;
   determining, by the processor, a second aggregate score based at least in part on one or more of the modified second scores, wherein the second aggregate score indicates a periodontal health state of the patient;
   determining, by the processor, a dental health score based on the first aggregate score and the second aggregate score, wherein the dental health score indicates an overall dental health of the patient; and
   outputting the dental health score to a display device.

17. The non-transitory computer-readable medium of claim 16, wherein each first set of data comprises a parameter specifying a number of surfaces of the tooth at the corresponding location that are damaged or missing; and
   wherein determining each first score is based on the number of surfaces of the tooth at the corresponding location that are damaged or missing.

18. The non-transitory computer-readable medium of claim 16, wherein determining the first aggregate score comprises:
   summing, by the processor, the first scores;
   selecting, by the processor, a particular hard tissue health category from among a plurality of hard tissue health categories based on the sum of the first scores; and
   determining, by the processor, the first aggregate score based on the selected hard tissue health category.

19. The non-transitory computer-readable medium of claim 18, wherein each second set of data comprises:
   an average crown length of the tooth at the corresponding location, an average root length of the tooth at the corresponding location, a gingival attachment length of the tooth at the corresponding location, a root tip length of the tooth at the corresponding location, and a combined attachment loss of the tooth at the corresponding location.

20. The non-transitory computer-readable medium of claim 16,
   wherein the indication that the tooth location is associated with the particular physical characteristic comprises an indication that the tooth at the location exhibits bleeding upon probing; and
   wherein modifying the initial second score for the tooth location comprises reducing the initial second score for the location by a pre-determined value.

21. The non-transitory computer-readable medium of 16,
   wherein the indication that the tooth location is associated with the particular physical characteristic comprises an indication that the tooth at the location exhibits suppuration; and
   wherein modifying the initial second score for the tooth location comprises reducing the initial second score for the location by a pre-determined value.

22. The non-transitory computer-readable medium of claim 16,
   wherein the indication that the tooth location is associated with the particular physical characteristic comprises an indication of a degree of mobility of the tooth at the location; and
   wherein modifying the initial second score for the tooth location comprises reducing the initial second score for the location by a pre-determined value.

23. The non-transitory computer-readable medium of claim 16,
wherein the indication that the tooth location is associated with the particular physical characteristic comprises an indication of a degree of furcation involvement of the tooth at the location; and
wherein modifying the initial second score for the tooth location comprises reducing the initial second score for the location by a pre-determined value.

24. The non-transitory computer-readable medium of claim 16,
wherein the indication that the tooth location is associated with the particular physical characteristic comprises an indication of a root to crown ratio of the tooth at the location; and
wherein modifying the initial second score for the tooth location comprises reducing the initial second score for the location by the modifier score.

25. The non-transitory computer-readable medium of claim 16, wherein determining the second aggregate score comprises:
determining, by the processor, an average of the modified second scores for each region of a plurality of regions of a patient's mouth, wherein each average of the modified second scores corresponds to teeth of a different respective region;
selecting, by the processor, a particular periodontal health category from among a plurality of periodontal health categories based on the averages of the modified second scores; and
determining, by the processor, the second aggregate score based on the selected periodontal health category.

26. The non-transitory computer-readable medium of claim 16, wherein determining the dental health score comprises adding, by the processor, the first aggregate score and the second aggregate score.

27. The non-transitory computer-readable medium of claim 16, wherein the instructions which, when executed by the one or more processors further causes:
determining, by the processor, a course of treatment for the patient based at least in part on the dental health score.

28. The non-transitory computer-readable medium of 27, further comprising outputting to a display the determined course of treatment as a recommended course of treatment.

29. The non-transitory computer-readable medium of claim 16, wherein the instructions which, when executed by the one or more processors further causes:
automatically generating, by the processor, a narrative describing the dental health of the patient based on the dental health score; and
outputting the narrative to a display device.

30. The non-transitory computer-readable medium of claim 29, wherein automatically generating the narrative comprises:
obtaining, by the processor, a plurality of narrative templates, each corresponding to a different dental health condition; and
automatically selecting, by the processor, at least one of the narrative templates based on the dental health score.

31. The method of claim 1, wherein, for each location of the plurality of tooth locations, the plurality of physical parameters of the tooth at the location comprises a crown length, a gingival attachment length, a root length, a root tip length, a recession, and a pocket depth of the tooth at the location.

32. The method of claim 1, wherein, for each location of the plurality of tooth locations, the plurality of physical parameters of the tooth at the location consists of a crown length, a gingival attachment length, a root length, a root tip length, a recession, and a pocket depth of the tooth at the location.

33. The method of claim 1, wherein, for each location of the plurality of tooth locations, the initial second score is determined based on an effective root percentage of one or more surfaces of the tooth at the location.

34. The method of claim 1, wherein, for each location of the plurality of tooth locations, determining the initial second score comprises:
determining, for each surface of plurality of surfaces of the tooth at the location, a respective effective root percentage, and
determining an average of the effective root percentages.

35. The method of claim 1, wherein the dental health score is a continuous numerical sequence, wherein a first portion of the continuous numerical sequence corresponds to the first aggregate score, and wherein a second portion of the continuous numerical sequence corresponds to the second aggregate score.

* * * * *